US012274284B2

United States Patent
Rischbieter et al.

(10) Patent No.: US 12,274,284 B2
(45) Date of Patent: Apr. 15, 2025

(54) HIGH-ENERGY FOOD SUPPLEMENT BASED ON INVERTED SUGARS AND ERGOGENIC PRODUCTS FOR USE IN PHYSICAL ACTIVITY AND METHOD FOR PRODUCING SAME

(71) Applicants: Ivo Rischbieter, Blumenau (BR); Ronaldo Biondo, São Caetano do Sul (BR)

(72) Inventors: Ivo Rischbieter, Blumenau (BR); Ronaldo Biondo, São Caetano do Sul (BR)

( * ) Notice: Subject to any disclaimer, the term of this patent is extended or adjusted under 35 U.S.C. 154(b) by 691 days.

(21) Appl. No.: 17/613,682

(22) PCT Filed: May 30, 2020

(86) PCT No.: PCT/BR2020/050192
§ 371 (c)(1),
(2) Date: Nov. 23, 2021

(87) PCT Pub. No.: WO2020/237340
PCT Pub. Date: Dec. 3, 2020

(65) Prior Publication Data
US 2022/0240558 A1    Aug. 4, 2022

(30) Foreign Application Priority Data

May 31, 2019  (BR) .................. 10 2019 011309-0
Apr. 8, 2020  (BR) .................. 13 2020 007001 0

(51) Int. Cl.
| A61K 36/00 | (2006.01) |
| A23L 33/125 | (2016.01) |
| A23L 33/155 | (2016.01) |
| A23L 33/16 | (2016.01) |
| A23L 33/175 | (2016.01) |
| A23L 33/185 | (2016.01) |
| A23L 33/19 | (2016.01) |
| C12P 19/02 | (2006.01) |
| C13K 3/00 | (2006.01) |

(52) U.S. Cl.
CPC ........... *A23L 33/125* (2016.08); *A23L 33/155* (2016.08); *A23L 33/16* (2016.08); *A23L 33/175* (2016.08); *A23L 33/185* (2016.08); *A23L 33/19* (2016.08); *C12P 19/02* (2013.01); *C13K 3/00* (2013.01); *A23V 2002/00* (2013.01)

(58) Field of Classification Search
None
See application file for complete search history.

(56) References Cited

U.S. PATENT DOCUMENTS

| 3,436,459 A | 4/1969 | La Roche |
| 4,220,666 A | 9/1980 | Fields |

FOREIGN PATENT DOCUMENTS

| BR | PI0414761 A | 11/2006 | |
| BR | PI0715018 A2 | 11/2013 | |
| BR | PI0908047 A2 | 8/2015 | |
| CN | 108925994 A | 12/2008 | |
| CN | 104055189 A | 9/2014 | |
| CN | 106834551 A | 6/2017 | |
| FR | 2972328 A1 | 9/2012 | |
| JP | 2002322062 A | 11/2002 | |
| WO | WO-2017147668 A1 * | 9/2017 | ............... C13K 3/00 |

OTHER PUBLICATIONS

Liquid Gel Orange, Dextro Energy. 2015. Disponivel em: htms://dextro-energj:.de/en/nroduct-lig,uid-gel/. Accessed on: Aug. 30, 2020.
Wellion Orange: xarope de a~ucar invertido. 2010. Disponivel em: https ://www.wellion.pt/pt/produtos/xarope de acuar invertido/wellion_orange/. Accessed on: Aug. 31, 2020.

* cited by examiner

*Primary Examiner* — Russell G Fiebig
(74) *Attorney, Agent, or Firm* — Muncy, Geissler, Olds & Lowe, P.C.

(57) ABSTRACT

The present invention relates to the production method and to compositions relating to a high-energy supplement/foodstuff based on inverted brown sugars originating primarily from sugar cane, providing advantages in response to exercise and superior sensory qualities in the opinion of athletes. The energy supplement/foodstuff, in liquid, gel or paste form, to which the present invention relates, has ideal nutritional compositions for combining this source of carbohydrates thrown sugars with equimolar proportions of glucose and fructose and a low concentration of sucrose) with other sources of carbohydrates, ergogenic products, vitamins, aromas, essential minerals, amino acids, proteins and other products of interest, with the aim of increasing physical performance for athletes or consumers in general.

5 Claims, No Drawings

HIGH-ENERGY FOOD SUPPLEMENT BASED ON INVERTED SUGARS AND ERGOGENIC PRODUCTS FOR USE IN PHYSICAL ACTIVITY AND METHOD FOR PRODUCING SAME

FIELD OF THE INVENTION

This invention refers to certificate of addition to BR 10 2019 011309 0, filed on May 31, 2019, and in particular to the formulation of several food compositions of high energy value, based on inverted sugars, preferably brown, demerara, VHP, and VVHP sugars, focused on athletes in general with various purposes. Using inverted sugar takes advantage of its important equimolar composition of glucose and fructose in a single product and also ensuring better physical performance in view of both types of carbohydrates. These are compositions used as a food supplement, playing the role of satisfying the energy demand before, during, and/or after physical exercise, based on enzymatically inverted carbohydrates and others through a natural process without chemical additives. In addition to its natural content, especially glucose and fructose, this product may be added with: minerals, aromas, vitamins, amino acids, proteins, ergogenic or thermogenic products, plant extracts, fatty acids, and others, as described in the state of the art.

The basic food composition of this invention is of plant origin (sugarcane), is intended for a sports line of products, and exhibits better sensorial characteristics than the energy products available on the market. Besides, as a result of its high concentration of different carbohydrates relatively to commercially available carbohydrates, for the same portion of product intake, the quantity of carbohydrates is higher as well as confers it a long shelf life with no conservatives added. This enables higher energy efficiency and allows for a reduced intake of the product, whether in short or long-duration exercises, before, during, and after the exercise. It can even be used as a food supplement for non-athletes wishing to increase their energy in occasional exercises.

BACKGROUND OF THE INVENTION

The search for a healthier life, with balanced nutrition combined with physical exercise, has been growing both among those who used to only care about aesthetics and other groups with a higher concern about health [Pereira R F. Conhecimentos de nutrição e hábitos alimentares de alunos de academias de ginástica na cidade de São Paulo. Master's Dissertation. University of São Paulo, 1999].

According to the World Health Organization, the proposed dietary consumption of macro nutrients is comprised of 55.0 to 75.0% carbohydrates, 15.0 to 30.0% lipids, and 10.0 to 15.0% proteins [World Health Organization (WHO). Diet, nutrition and the prevention of chronic diseases. Report of a joint WHO/FAO expert consultation. Geneva; 2003. WHO—Technical Report Series, 916]. However, there is still a huge lack of reliable information about nutrition, which leads those who work out to keep inappropriate dietary habits or to erroneously consume food supplements, jeopardizing the achievement of their goals with physical exercise [ADA Reports. Position of the American Dietetic Association, Dietitians of Canada, and the American College of Sports Medicine: Nutrition and the athletic performance. J Am Diet Assoc 2000; 100 (12): 1543-556; Blanco B, Suarez S. Gimnasios: um mundo de información para la confusión em nutrición. Annais Venezolanos de Nutrición 1998; 11(1): 55-65; Pereira R F, Lajolo F M, Hirschbruch M D. Consumo de suplementos por alunos de academias de ginástica em São Paulo. Rev Nutr. 2003; 16 (3): 265-72].

Physical exercise is a condition in which a quick energy mobilization and redistribution takes place to perform the muscular work. The organic functions performed are primarily due to the chemical energy deriving from the metabolization of the nutrients taken in from nutrition, to generate adenosine triphosphate (ATP), the fuel used in all cell reactions.

Carbohydrate metabolism plays a key role in supplying energy for physical activity and physical workout. In high-intensity exercises, the largest part of the energy demand is fulfilled by the energy from the breakdown of carbohydrates. They become available to the organism through diet, are stored in the form of muscular and hepatic glycogen, and their shortage leads to fatigue [Maughan S M, et al. Bioquímica do exercício e do treinamento. São Paulo, Manole, 2000, 241 p.].

Hepatic glycogen plays the role of maintaining the blood sugar level between meals, working as a glucose reserve for the energy needs of the brain, the nervous system, and other tissues. Muscular glycogen, on the other hand, is used by the muscle itself as a source of energy in muscle contraction [Soares E A, Ferreira A M D, Ribeiro, B G. Consumo de carboidratos e lipídeos no desempenho em exercícios de ultra-resistência. Rev Bras Med Esporte, 7: 67-74, 2001].

Glycogen is a polysaccharide made up of thousands of glucose units.

As the carbohydrates present in food are digested by the human metabolism, they are absorbed by the intestine and are carried by the blood to all tissues. Thus, the amount of glucose circulating in the blood becomes higher. When this quantity becomes higher than the organic needs, this "surplus" is stored in the form of glycogen. As the quantity of glucose circulating in the blood is reduced, the glycogen stored breaks down into glucose, allowing the quantity of that substance not to reach very low levels (hypoglycemia).

The mechanism of the muscle glycogen balance shows a linear correlation between body fatigue time and the concentrations of glycogen in the muscle, and it tends to be difficult to maintain the workout intensity when the glycogen is on low levels in the muscle [Lima-Silva A E, Fernandes T C, Oliveira F R, Nakamura F Y, Gevaerd M S. Metabolismo do glicogênio muscular durante o exercício físico: mecanismos de regulação. Ver Nutr Campinas, 20, 417-429, 2007].

The fatigue taking place in prolonged, high-intensity physical exercise is mostly associated with low stocks and depletion of glycogen, hypoglycemia, and dehydration. As the stocks of carbohydrates are limited in the organism, keeping a diet with food rich in carbohydrates is key to muscle and hepatic replenishment, as well as to the immune response. However, several factors such as the nutritional state and training; the type, quantity, time, and frequency of carbohydrate intakes affect the restoration of glycogen [Coelho C F, Sakzenian V M, Burini R C. Ingestão de carboidratos e desempenho físico. Ver Nutr Pauta, 4: 67, 51-56, 2004].

Thus, an adequate availability of carbohydrates is indispensable to the training and successful athletic performance. As the energy expenditure during the exercise increases by 2 to 3 times, the distribution of macro nutrients from the diet is modified in active individuals and in athletes [Matsudo S M. Nutrição, atividade física e desempenho. Ver Nutr Pauta, 2: 31-37, 2001].

Athletes should consume more carbohydrates than as recommended for less active people, which corresponds to 60 to 70% of the total calorie value. An intake from 5 to 10 g/kg/day of carbohydrates is recommended depending on the type and duration of the physical exercise chosen and the specific characteristics of the individual, such as hereditary traits, gender, age, weight and body composition, physical conditioning, and the training phase. The recommended calorie intake needs are between 37 and 41 kcal/kg of weight a day, and, depending on the goals, varying from 30 to 50 kcal/kg/ of weight a day [Sociedade Brasileira de Medicina do Esporte, 2003].

Carbohydrates are important energetic substrates for muscle contraction during prolonged exercise done with moderate intensity and in high-intensity, short-duration exercises. Using nutritional strategies involving a diet rich in carbohydrates before performing physical exercises increases the glycogen reserves, both muscular and hepatic. An intake of carbohydrates during the effort, on the other hand, helps maintain the blood sugar level and oxidation of these substrates. Following the effort, the intake of carbohydrates aims to replenish the depleted stocks and ensure an anabolic pattern [Cyrino E S, Zucas S M. Influência da ingestão de carboidratos sobre o desempenho físico. Rev Ed Fis/UEM 10:1: 73-79, 1999].

According to Maughan and collaborators [Maughan S M, et al. Bioquímica do exercício e do treinamento. São Paulo, Manole, 2000, 241 p.], the glycogen content existing in the skeletal muscle is approximately 14 to 18 g per kilogram of wet mass (approximately a total of 250 to 400 g in the muscles).

The liver also has glycogen; between 80 and 110 g are stored in the liver of an adult human being in a post-absorbed state and can be released into the circulation to keep the blood concentration of glucose at more or less 0.9 g per liter.

Such values may be modified as per the level of training of the individual, associated with an intake of diets rich in carbohydrates [Biesek S, Alves, L A, Guerra, I. Estratégias de nutrição e suplementação no esporte. Editora Manole, $1^{st}$ Brazilian Edition, 2005]. In strength exercises, physical training associated with the use of diets rich in carbohydrates may provide an increase in the muscle glycogen reserves, speeding up the process of muscle mass building (hypertrophy) [Cyrino E S, Zucas S M. Influência da ingestão de carboidratos sobre o desempenho físico. Rev Ed Fis/UEM 10:1: 73-79, 1999].

According to Coyle [Coyle, E F. Altos e baixos das dietas à base de carboidratos. Esports Sci Exchange. São Paulo, 2005], athletes and non-athletes are interested in food information that is simple, handy, and easy so that they can achieve their physical goals. Scientific studies claim that the quantity and type of carbohydrate should vary directly according to the intensity and volume of workout.

The higher the intensity of the exercises, the larger the participation of carbohydrates will be as energy suppliers.

Prolonged exercise highly reduces the concentration of muscle glycogen and requires a constant concern about its replenishment; however, in spite of such verification, a low consumption of carbohydrates by individuals doing physical activity [Carvalho T. Modificações dietéticas, reposição hídrica, suplementos alimentares e drogas: comprovação de ação ergogênica e potenciais riscos para a saúde. Rev Bras Med Esporte, 9: 2, 43-56, 2003]. Restricting carbohydrates in diet determines ketosis and a loss of muscle proteins, accumulated lactate, causing damage to the muscle from the reduced pH, and can be lethal to cells and contribute to an early fatigue process [Sahlin, k. Metabolic factors of fatigue. Sports Medicine, 13, 99-107, 1992].

According to Coyle [Coyle, E F. Altos e baixos das dietas à base de carboidratos. Esports Sci Exchange. São Paulo, 2005], individuals who take in a diet poor in carbohydrates should exhibit reduced tolerance to exercise, as well as compromised ability to improve their physical resistance through training.

In a study conducted with young men doing physical activity twice to 4 times a week, for seven days, comparing a diet rich in carbohydrates to a diet poor in carbohydrates, it was found that the diet poor in carbohydrates is harmful to those doing long-duration physical activity.

On top of all the discussion on the biochemistry of carbohydrates, the search for mechanisms to increase the performance of individuals doing physical activity has been growing at a fast pace. Other mechanisms, associated with ERGOGENIC AIDS, have drawn more and more attention. Such aids are divided into 5 categories, nutritional, pharmacological, physiological, psychological, and mechanical [Tirapegui J. Nutrição, metabolismo e suplementação na atividade física. $2^{nd}$ ed. São Paulo: Atheneu, 2012; Guerra I, Biesek S, Alves L. Estratégias de Nutrição e Suplementação no Esporte—$3^{rd}$ ed. São Paulo: Manole, 2015; Pereira, L. P. Utilização de recursos ergogênicos nutricionais e/ou farmacológicos em uma academia da cidade de Barra do Piraí, R J. Rev. Bras. Nutr. Esp. 8: 58-64, 2014].

Within that context, nutritional ergogenic aids exhibit significant relevance, since their inadequate use is associated with potential risks to users.

Ergogenic aids are defined as mechanisms capable of improving the performance of individuals doing physical activity through physical power, mental strength, or mechanical advantage [Tirapegui J. Nutrição, metabolismo e suplementação na atividade física. $2^{nd}$ ed. São Paulo: Atheneu, 2012; Guerra I, Biesek S, Alves L. Estratégias de Nutrição e Suplementação no Esporte—$3^{rd}$ ed. São Paulo: Manole, 2015].

In this regard, using some nutritional supplements with an ergogenic potential has been proven to be an efficient way of postponing the occurrence of fatigue and increasing the contractile power of the skeletal and/or cardiac muscle, thus optimizing the ability to perform physical work, that is, physical performance [Applegate E. Effective nutritional ergogenic aids. Int J Sports Nutr 9(2): 229-239, 1999; Clarkson P M. Nutrition for improved sports performance. Current Issues on ergogenic aids. Sports Med 21(6): 393-401, 1996; Williams M N. Nutritional ergogenics in athletics. J Sports Sci 13: S63-74, 1995].

According to Lemon [Lemon P W R. Effects of exercise on dietary protein requirements. Int J Sports Nutr 8(4): 426-47, 1998], people involved in resistance training need 1.2 to 1.4 g protein per kilogram of weight a day, whereas strength athletes need 1.6 to 1.7 g/kg of weight/day, well above the 0.8 to 1.0 g/kg of weight/day established for physically inactive individuals. An intake of protein or amino acids following physical exercises favors muscle protein synthesis and recovery [Børshein E, Aarsland A, Wolfe, R R. Effect of amino acids, protein, and carbohydrate mixture in net muscle protein balance after resistance exercise. Int J Sports Nutr Exer Metab 14(3): 255-71, 2004; Lemon P W R. Effects of exercise on dietary protein requirements. Int J Sports Nutr 8(4): 426-47, 1998].

Taking into account nutritional ergogenic aids, protein aids are widely used nowadays. According to studies with athletes reported by Vieira and Biesek [Vieira A C S, Biesek S. Avaliação do consumo de recursos ergogênicos nutricionais por praticantes de artes marciais em uma academia da cidade de Curitiba/PR. Rev Bras Nutr Esp 09: 454-462, 2015] and Peçanha et al. [Peçanha M A C, Navarro F, Maia T N. O consumo de suplementos alimentares por atletas de culturismo. Rev Bras Nutr Esp 09: 215-222, 2015], approximately 63.6% to 100.0% of the athletes assessed used protein aids, including, as the most widely used ones, whey protein and BCAAs, reaching values of 72.7% to 75.0% of use.

The daily protein intake recommendations for athletes depend on the level of training and the intensity and duration of the workouts, consisting of 1.2 to 1.7 g/kg of body weight or 12% to 15% of the total energy consumption. Endurance (resistance) athletes involved in moderate-intensity training need a protein intake of 1.1 g/kg/day, whereas elite endurance athletes may require as high as 1.6 g/kg/day. On the other hand, strength athletes may need 1.6 to 1.7 g/kg/day of protein [Terada L C, Godoi M R, Silva T C V, Monteiro T L. Efeitos metabólicos da suplementação do Whey Protein em praticantes com pesos. Rev Bras Nutr Esp 3: 295-304, 2009].

Carbohydrates

The carbohydrates used to manufacture most of the supplements used for athletes that are currently available on the market are generally based on dextrose and maltodextrins produced from corn starch. However, several carbohydrates may be used for that purpose:

Sucrose: is a disaccharide made up of glucose and fructose. Its intake varies from 14 to 60 g/day, with an average of 41 g/day. It supplies 4 Kcal/g. [ADA Reports. Position of the American Dietetic Association: use of nutritive and non-nutritive sweeteners. J Am Diet Assoc 104 (2):255-75, 2004. Erratum in: J Am Diet Assoc 104(6):1013, 2004].

Fructose: is a monosaccharide found especially in fruit. It is found as a component of corn syrups rich in fructose. Crystalline fructose is obtained from corn starch through isomerization. It supplies 4 Kcal/g. Its metabolism does not depend on insulin. The acceptable daily dose is a maximum of 50 g/day [Livesey G, Taylor R. Fructose consumption and consequences for glycation, plasma triacylglycerol, and body weight: meta analyses and meta-regression models of intervention studies. Am J Clin Nutr 88(5):1419-37, 2008].

Glucose or dextrose: is a monosaccharide found in fruit, vegetables, and in the breakdown of various starches. Absorbed in the small intestine. It has a lower sweetening effect than sucrose. It supplies 4 Kcal/g [Tumas R, Goastico S S V, Gandolfo A S. Adoçantes. In: Delgado A F, Cardoso A L, Zamberlan P. Adoçantes em nutrologia básica e avançada. São Paulo: Manole; 2010].

Lactose: is the milk sugar and a disaccharide made up of one glucose molecule and one galactose molecule. It may lead to intestinal fermentation in individuals with a lactase deficiency. It supplies 4 Kcal/g [Tumas R, Goastico S S V, Gandolfo A S. Adoçantes. In: Delgado A F, Cardoso A L, Zamberlan P. Adoçantes em nutrologia básica e avançada. São Paulo: Manole; 2010].

Polyols: sorbitol, mannitol, erythritol, and xylitol are less caloric than sucrose, glucose, and fructose and supply from 1.6 to 2.6 Kcal/g. Sorbitol further has the advantage of stimulating motility of the biliary vesicle, however, as polyols have incomplete intestine absorption, they may lead to diarrhea conditions [ADA Reports. Position of the American Dietetic Association: use of nutritive and non-nutritive sweeteners. J Am Diet Assoc 2004, 104 (2):255-75. Erratum in: J Am Diet Assoc 104(6):1013, 2004; Joint FAO/WHO Expert Committee on Food Additives. Toxicological evaluation of certain food additives: sorbitol. Twenty-sixth report. Geneva: WHO; 1982. p. 218-28. WHO—Technical Report Series, 683].

Maltodextrins: currently, the most widely used carbohydrate for athlete supplementation [Rankin J W. Efeito da ingestão de carboidratos no desempenho de atletas em exercícios de alta intensidade. Gatorade Sports Science Institute, 2001], is a complex carbohydrate coming from starch conversion, generally corn, used in several industrialized products. It is frequently suggested that there are differences in the rate of digestion and absorption of maltodextrins compared to glucose. While glucose is immediately available for absorption upon arrival to the small intestine [Man C, Camilleri M, Cobelli, C. A system model of oral glucose absorption: validation on gold standard data. Biomed. Eng IEEE Trans On 53: 2472-2478, 2006], maltodextrins need to be digested by α-amylase and by maltase first, resulting in a lower glycemic response [Zhang G, Hamaker B R. Slowly digestible starch: concept, mechanism, and proposed extended glycemic index. Crit Rev Food Sci Nutr 49: 852-867, 2009]. This assertion is however controversial, since enzymatic digestion of maltodextrins seems to occur at a high rate, leading to an absorption rate that is different from the absorption of pure glucose [Hawley J A, Dennis S C, Noakes T D. Oxidation of carbohydrate ingested during prolonged endurance exercise. Sports Med 14: 27-42, 1992; Wagenmakers A J, Brouns F, Saris W H, Halliday D. Oxidation rates of orally ingested carbohydrates during prolonged exercise in men. J Appl Physiol 75: 2774-2780, 1993; Jeukendrup A E. Carbohydrate intake during exercise and performance. Nutrition 20:669-677, 2004].

It has been demonstrated that a combination of maltodextrins with proteins and/or amino acids may promote an increase in glycogen recovery and stimulate the synthesis of muscle protein following an intensive exercise protocol [Costill D L, Hargreaves M. Carbohydrate nutrition and fatigue. Sports Med 13: 86-92, 1992; Shi X, Summers R W, Schedl H P, Flanagan S W, Chang R, Gisolfi, C V. Effects of carbohydrate type and concentration and solution osmolality on water absorption. Med Sci Sports Exer 27:1607, 1995; Kerksick C, Harvey T, Stout J, Campbell B, Wilborn C, Kreider R, Kalman D, Ziegenfuss T, Lopez H, Landis J. International Society of Sports Nutrition position stand: Nutrient timing. J Int Soc Sport Nutr 5:17, 2008]. Maltodextrins stand out for offering excellent results in sports nutrition. In addition to not causing sudden increases in blood sugar levels, they avoid undesired secondary effects, such as early depletion of hepatic glycogen and increased levels of uric acid, cholesterol, and triglycerides. [http://aditivosingredientes.com.br/upload_arquivos/201603/20160300463470014 59191801.pdf].

Other carbohydrates and biomaterials such as: maltose, mannose, fruit syrups (e.g. apple syrup), coconut syrup, beetroot sugar (sucrose), Palatinose (isomaltulose), ribose, leucrose, xylose, trehalose, cellobiose, arabinose, cyclodextrins, chitins and chitosans, royal jelly, bee honey, vegan honey, propolis, fructooligosaccharides (FOS), and others, are potential components of various formulations in supplements.

The next topics describe in short the main products used as ergogenic in sports supplementation products:

Branched Chain Amino Acids (BCAA)

Branched chain amino acids, commonly known as BCAA, cover three essential amino acids, that is, those that are not endogenously synthesized by the body, that is: leucine, isoleucine, and valine [Gonçalves L A. A suplementação de leucina corn relação à massa muscular ern humanos. Rev Bras Nutr Esp 07: 212-223, 2013].

Six amino acids may be oxidized by the skeletal muscle, namely: leucine, isoleucine, valine, glutamate, aspartate, and asparagine, however, the BCAAs (leucine, isoleucine, and valine) are preferably oxidized [Júnior M P. Aspectos atuais sobre aminoácidos de cadeia ramificada e seu efeito ergogênico no desempenho físico humano. Rev Bras Nutr Esp, v. 06: 436-448, 2012; Gonçalves L A. A suplementação de leucina corn relação à massa muscular ern humanos. Rev Bras Nutr Esp 07: 212-223, 2013; Wlock C L, Schneider G, Souza P C, Liberali R. Suplementação de aminoácidos de cadeia ramificada (AACR) e seu efeito sobre o balanço proteico muscular e a fadiga central ern exercícios de endurance. Rev Bras Nutr Esp 02: 250-264, 2008].

More recent studies have suggested that the same promote a reduction in central fatigue during prolonged exercise [Júnior M P. Aspectos atuais sobre aminoácidos de cadeia ramificada e seu efeito ergogênico no desempenho físico humano. Rev Bras Nutr Esp, v. 06: 436-448, 2012], a condition that can be associated with peripheral and central factors, dependent on nutrient consumption, level of training, and intensity and duration of the workouts done by the individual [Rogero M M, Tirapegui J. Aspectos atuais sobre os aminoácidos de cadeia ramificada. Rev Bras Ciênc Farm 44, No. 44, 2008].

On top of that, BCAAs are widely used by individuals engaged in physical activity on the assumption that they may promote muscle protein anabolism, reduce the degree of muscle injury caused by the practice of physical exercises [Júnior, M. P. Efeito da suplementação de aminoácidos de cadeia ramificada no desempenho físico humano. Rev Bras Nutr Esp 10: 157-164, 2016], make insulin release easier, and improve the user's performance. On top of that, they are sources of nitrogen for a synthesis of two other amino acids, alanine and glutamine [Júnior M P. Aspectos atuais sobre aminoácidos de cadeia ramificada e seu efeito ergogênico no desempenho físico humano. Rev Bras Nutr Esp, v. 06: 436-448, 2012].

The daily recommendation of branched chain amino acids for adults according to the FAO/WHO (2011) is 20 mg/kg of isoleucine, 26 mg/kg of valine, and 39 mg/kg of leucine. According to Kleiner [Kleiner S M, Robinson M G., translation by Kelbert, R. Nutrição para o treinamento de força. $3^{rd}$ ed. —Barueri, S P: Manole, 2009], daily doses of 4 to 21 g of BCAA during the training and 2 to 4 g/h with a solution of glucose and electrolytes at 6 to 8% before and during prolonged exercise improved physiological and psychological responses to the training.

Isolated Leucine

Of all three amino acids comprising BCAA, leucine has the highest oxidation rate compared to the other two and, for that reason, it is a more frequent target of investigations [Júnior M P. Aspectos atuais sobre aminoácidos de cadeia ramificada e seu efeito ergogênico no desempenho físico humano. Rev Bras Nutr Esp, v. 06: 436-448, 2012]. Moreover, leucine has also been drawing attention due to its physiological properties [Gonçalves L A. A suplementação de leucina corn relação à massa muscular em humanos. Rev Bras Nutr Esp 07: 212-223, 2013].

It is pointed out as a regulator of the metabolic processes involving the synthesis and breakdown of the muscle protein [Júnior M P. Aspectos atuais sobre aminoácidos de cadeia ramificada e seu efeito ergogênico no desempenho físico humano. Rev Bras Nutr Esp, v. 06: 436-448, 2012]. Accordingly, it has been demonstrating a promising effect in atrophy therapy by acting to inhibit the proteolysis caused by the catabolic state when the training is intensive [Gonçalves L A. A suplementação de leucina corn relação à massa muscular em humanos. Rev Bras Nutr Esp 07: 212-223, 2013]. The same amino acid is deemed associated with the release of gluconeogenic precursors, such as alanine, through the skeletal muscle [Júnior M P. Aspectos atuais sobre aminoácidos de cadeia ramificada e seu efeito ergogênico no desempenho físico humano. Rev Bras Nutr Esp, v. 06: 436-448, 2012]. According to the FAO/WHO (2011), a normal individual needs 39 mg/kg of leucine on a daily basis.

A leucine metabolite known as β-hydroxy-β-methylbutyrate (HMB) has been used in supplementation for athletes showing an increase in muscle mass with doses from 1.5 to 3.0 g/day in the training [Kerksick C M, et al. ISSN exercise & Sport nutrition review update: research & recommendations. J Inter Soc Sport Nutr, 15: 38, 2018].

Whey Protein

Athletes, people engaged in physical activity, physically active people, and even people with diseases have been seeking benefits in that protein source.

Recent evidence has supported the theory that the milk proteins, including whey proteins, on top of their high biological value, have bioactive peptides, which act as antimicrobial agents, anti-hypertensive agents, immune function regulators, as well as growth factors [Salzano Jr I. Nutritional supplements: practical applications in sports, human performance and life extension. Symposium series 007; São Paulo; 1996-2002. p. 75-202; Groziak S M, Miller G D. Natural bioactive substances in milk and colostrum: effects on the arterial blood pressure system. Brit J Nutr 84(6):119-25, 2000; Lönnerdal B. Nutritional and physiologic significance of human milk proteins. Am J Clin Nutr 77(6):1537-43, 2003].

The whey protein concentrate (WPS) has a protein concentration from 25% to 89%. In these products, non-protein components are removed, causing an increase in the protein content and a reduction in the sugar present in the milk [Carrilho L H. Benefícios da utilização da proteína do soro de leite Whey Protein. Rev Bras Nutr Esp 7: 195-203, 2013]. The whey protein isolate (WPI) contains from 90.0% to 95.0% protein, with fat and lactose in a minimum proportion or even not present. Hydrolyzed whey protein, however, corresponds to an isolated and concentrated fraction that is broken down into peptides of high nutritional value and high digestibility and absorption [Carrilho L H. Benefícios da utilização da proteína do soro de leite Whey Protein. Rev Bras Nutr Esp 7: 195-203, 2013].

Whey Protein is a widely used supplement in sports that can promote muscle hypertrophy [Carrilho L H. Benefícios da utilização da proteína do soro de leite Whey Protein. Rev Bras Nutr Esp 7: 195-203, 2013; Souza L B L, Palmeira M E, Palmeira E O. Eficácia do use de Whey Protein associado ao exercício, comparada a outras fontes proteicas sobre a massa muscular de indivíduos jovens e saudáveis. Rev Bras Nutr Esp 9: 607-613, 2015]. Present in all milk types, bovine whey protein contains around 80% casein and 20% serum proteins. When proteins are made up of: beta-lactoglobulin (BLG), alpha-lactalbumin (ALA), bovine serum albumin (BSA), immunoglobulins (IGs), and glycomacropeptides (GMP).

There are different ways in which whey protein helps with muscle hypertrophy: a) it promotes an increase in leucine concentrations, which favors muscle anabolism [Carrilho L H. Benefícios da utilização da proteína do soro de leite Whey Protein. Rev Bras Nutr Esp 7: 195-203, 2013]; b) because it has its protein composition similar to the proteins of the skeletal muscle, supply almost all amino acids in a similar proportion to the skeletal muscle, which constitutes an actual value as an anabolic supplement [Ha E, Zemel M B. Functional properties of Whey, Whey components, and essential amino acids: mechanisms underlying health benefits for active people. J Nutr Biochem.; 14: 251-58, 2003].

In the studies conducted by Carrilho [Carrilho L H. Benefícios da utilização da proteína do soro de leite Whey Protein. Rev Bras Nutr Esp 7: 195-203, 2013] whey protein supplementation promoted a significant reduction in the body fat, increased muscle mass and strength, increased hepatic and muscular glycogen, and an increase in the mineral bone density with no adverse conditions present.

Calbet and MacLean [Calbet J A L, MacLean D A. Plasma glucagon and insulin responses depend on the rate of appearance of amino acids after ingestion of different protein solutions in humans. J Nutr 132:2174-82, 2002] assessed the effect of four different solutions, one containing only 25 g/L glucose (C) and three containing 25 g/L glucose with 0.25 g/kg of body weight from three different protein sources: peas, whey proteins, and whole milk on the concentrations of insulin and amino acids. They observed that, 20 minutes after ingestion, the solution containing whey proteins caused a significant elevation in the plasma concentration of insulin ($p<0.05$). That elevation was approximately twice as large as the one observed with the solution containing whole milk and four times as large as the solution containing glucose only. They also observed that, after 20 minutes, the solution with whey caused a higher elevation in the plasma concentration of essential amino acids, primarily the BCAA, than with the other solutions. The increase in the BCAA concentration induced by whey proteins may also act by inhibiting muscle protein degradation [Werustsky C A. Inibição da degradação proteica muscular em atletas pela suplementação de aminoácidos. Nutrição Enteral e Esportiva 6:4-7, 1993].

Layman and collaborators, in their many studies [Layman D K. The role of leucine in weight loss diets and glucose homeostasis. J Nutr 133(1): 261-7, 2003; Layman D K, Baum J I. Dietary protein impact on glycemic control during weight loss. J Nutr 134(4): 968s-73s, 2004; Layman D K, Shiue H, Sather C, Erickson D, Baum J. Increased dietary protein modifies glucose and insulin homeostasis in adult woman during weight loss. J Nutr; 133(2):405-10, 2003], have shown that diets with a higher protein/carbohydrate ratio are more efficient to control the blood sugar level and insulin, thus favoring a reduction in body fat and preserved muscle mass during the weight loss process.

The above references have further shown that it is still necessary to develop a composition that advantageously combines a source of carbohydrates and proteins for the purpose of improving exercise performance.

Creatine

Creatine is an organic compound derived from the amino acids L-glycine, L-arginine, and L-methionine, called methyl-guanidinoacetic acid, which are present in our brain and muscle fibers with their synthesis taking place initially in the kidney, where glycine and arginine undergo a change and are transformed into guanidinoacetate, due to the action of the transaminase enzyme [TERENZI, G. A creatina como recurso ergogênico em exercícios de alta intensidade e curta duração: Uma revisão sistemática. Rev Bras Nutr Esp 7: 91-98, 2013].

Studies conducted by Souza and collaborators [Souza Junior T P, Dubas J P, Pereira B, Oliveira P R O. Suplementação de creatina e treinamento de força: alterações na resultante de força maxima a oito semanas de treinamento de força (hipertrofia). Rev Bras Med Esporte, 13: 303-309, 2007] and Volek and collaborators [Volek J S, Ratamess N A, Rubin M R, Gómez A L, French D N, McGuigan M M, Scheett T P, Sharman M J, Hakkinen K, Kraemer W J. The effects of creatine supplementation on muscular performance and body composition responses to short-term resistance training overreaching. Eur J Appl Physiol 91:628-37, 2004] showed that supplementation with creatine considerably increased strength relatively to the control group and evidenced that the body mass and fat-free mass in the legs were higher in the group using creatine.

Carvalho and collaborators [Carvalho F P P, Molina E G, Fontana E K. Suplementação com creatina associada ao treinamento resistido não altera as funções renal e hepática. Rev Bras Med Esp 17: 4, 2011] conducted a study for the purpose of assessing individuals under creatine supplementation to check for any changes in their kidney and liver functioning. Its duration was eight weeks of muscle training (resisted exercises). The study concluded that supplementation with creatine at the doses used (0.03 g/kg and 5 g/day) combined with training with resisted exercises does not change the kidney or liver function in the studied sample. At the 0.03 g/kg dose, creatine saturation (20 g/day for 5-7 days) leads to an increase in the concentrations of muscle creatine, and ever since then this protocol has begun to be used to check for the effect of this supplementation on athlete performance [Falção M E L. Saturação de creatina em indivíduos fisicamente ativos: Técnica eficaz ou desnecessária? Rev Bras Nutr Esp 10: 327-334, 2016]. Case reports suggest that creatine may be a potential nephrotoxic agent and, therefore, its use must be under professional supervision.

According to Kerksick and peers, creatine is regarded as the most effective nutritional supplement for athletes aiming to increase workout intensity and muscle mass [Kerksick C M, et al. ISSN exercise & Sport nutrition review update: research & recommendations. J Inter Soc Sport Nutr, 15: 38, 2018].

Glutamine

Glutamine is classified as a non-essential amino acid, that is, it is synthesized by our organism, however, under certain hypercatabolic clinical conditions, it is deemed a conditionally essential amino acid, since the glutamine synthesis is unable to meet the demands of the organism [Cruzat F V, Alvarenga L M. Metabolismo e suplementação com glutamine no esporte. Rev Bras Nutr Esp 0: 242-253, 2010; Paula L S, Santos D, Oliveira M D. Glutamine como recurs ergogênico na prática do exercício físico. Rev Bras Nutr Esp 9: 261-270, 2015]. Approximately 60% of free amino acids in the body are in the form of glutamine.

Glutamine supplementation before, during, and after exercise, whether exhaustive or not, has been studied with a view to attenuating the catabolic effects associated with a reduction in the glutamine concentration both in humans and in experimental models [Cruzat F V, Alvarenga L M. Metabolismo e suplementação com glutamine no esporte. Rev Bras Nutr Esp 0: 242-253, 2010; Vanelli B, Stragliotto K L, Lupion R. Uso da glutamine nas diferentes atividades físicas: Um estudo de revisão sistemática. Rev Bras Nutr Esp 09: 403-410, 2015].

Glutamine supplementation in resistance and strength athletes aims to promote cell anabolism, reduce catabolism, and fight immunosuppression conditions [Paula L S, Santos D, Oliveira M D. Glutamine como recurso ergogênico na prática do exercício físico. Rev Bras Nutr Esp 9: 261-270, 2015].

Under stressful conditions, such as high-intensity physical activity, the intracellular and plasma concentration of that amino acid is reduced by half, thus establishing a situation of deficiency [Paula L S, Santos D, Oliveira M D. Glutamine como recurso ergogênico na prática do exercício físico. Rev Bras Nutr Esp 9: 261-270, 2015].

Several studies have pointed out that oral glutamine supplementation increases the serum concentration and saves muscle energy substrates, which promotes improved performance for high-performance athletes in long-duration physical activities [Paula L S, Santos D, Oliveira M D. Glutamine como recurso ergogênico na prática do exercício físico. Rev Bras Nutr Esp 9: 261-270, 2015].

Hoffman and collaborators [Hoffman J R, Ratamess N A, Kang J, Rashti S L, Kelly N, Gonzalez A M, et al. Examination of the Efficacy of Acute L-alanyl-glutamine Ingestion During Hydration Stress in Endurance Exercise. J Int Soc Sport Nutr 7: 2-12, 2010] have found ergogenic effects from supplementation with glutamine, with increased exhaustion time, which may have been mediated by the improved absorption of electrolytes and fluids.

Arginine

Oral administration of arginine has been associated with an improvement in physical performance due to a likely reduction in muscle fatigue. This effect is allegedly associated with the vasodilation promoted by the nitric oxide, resulting in increased muscle perfusion, and by a reduction in the glucose consumption by the skeletal muscles that are active. Production of nitric oxide in the human organism takes place when the L-arginine amino acid is converted into L-citrulline. As a prolonged administration of arginine increases the production of nitric oxide, its supplementation has been associated with an improved contractile function of the skeletal muscle [Angell G, Barros L T, Barros L F D, Lima M. Investigação dos efeitos da suplementação oral de arginina no aumento de força e massa muscular. Rev Bras Nutr Esp 13: 2, 2007].

L-arginine as the precursor of nitric oxide has been used as an ergogenic aid in the world of sports in both endurance and strength training for the purpose of improving the aerobic capacity, reducing fatigue, and improving muscle hypertrophy.

Extraordinary effects exist from the use of that supplement, such as the "permanently pumped" effect (after 5-7 days of use), which consists in a kind of muscle volumization that literally will not disappear.

Unlike the volumization induced by exercise, which quickly disappears, permanent pumping is virtually perpetual; more speed in muscle contractions; increased strength of muscle contraction and the training load; higher resistance to and readiness for training; quick and complete muscle recovery following training; natural and without side effects [Ferreira A S, Gomes M P R, Navarro C A. Atuações do óxido nítrico e da suplementação de L-arginina nas respostas hemodinâmicas e metabólicas do organismo diante da prática do exercício físico. Rev Bras Nutr Esp 02: 364-373, 2008].

Agmatine, an arginine byproduct, has been associated with the insulin release flow, glucose consumption, hormone secretion, and neuronal nitric oxide pathway signaling. Another molecule that is also a precursor of arginine, known as citrulline, has also been used aiming at performance. However, there is no scientific evidence that it is associated with an increase in muscle mass and physical performance [Kerksick C M, et al. ISSN exercise & Sport nutrition review update: research & recommendations. J Inter Soc Sport Nutr, 15: 38, 2018].

β-Alanine

β-alanine is acquired by consuming food such as red meat and poultry; its endogenous production is performed in the liver [Trexler T E, Smith-Ryan A E; Stout J R, Hoffman J R, et al. International society of sports nutrition position stand: β-alanine. J Int Soc Sport Nutr 12: 30, 2015].

According to Culbertson and collaborators [Culbertson J Y, Kreider R B, Greenwood M, Cooke M. Effects of beta-alanine on muscle carnosine and exercise performance: a review of the current literature. Nutrients 2(1):75-98, 2010], β-alanine supplementation promoted a significant increase in the levels of intramuscular carnosine, which corresponds to improvements in workout performance.

Carnosine is known to be an antioxidant capable of preventing a buildup of oxidized products derived from lipid components of the biological membranes. This antioxidant has further shown to be effective to reduce lipid peroxidation, reducing oxidative stress when combined with aerobic exercises in men and women [Trexler T E, Smith-Ryan A E; Stout J R, Hoffman J R, et al. International society of sports nutrition position stand: β-alanine. J Int Soc Sport Nutr 12: 30, 2015].

According to Trexler and collaborators [Trexler T E, Smith-Ryan A E; Stout J R, Hoffman J R, et al. International society of sports nutrition position stand: β-alanine. J Int Soc Sport Nutr 12: 30, 2015], doses of 4-6 g/day of β-alanine in resistance athletes led to an increase in muscle carnosine concentrations by as high as 64% following 4 weeks, and after 10 weeks they increased by 80%, thus working as an intracellular pH buffer.

On the other hand, Saunder and collaborators [Saunders B, Elliott-Sale K, Artioli G G, et al. β-alanine supplementation to improve exercise capacity and performance: a systematic review and meta-analysis. Br J Sports Med 51:658-669, 2017] observed that β-alanine supplementation is capable of improving performance in various workout protocols, whether high-intensity continuous exercises or multiple intermittent series of efforts and exercise modalities.

N-Acetylcysteine

N-acetylcysteine is an acetylated form of the cysteine amino acid. It has a great antioxidant power, since it contains a thiol group (—SH). This form of cysteine is very stable and is used to reduce oxidative stress. In the human organism, N-acetylcysteine is converted into the antioxidant enzyme glutathione, a cell-protecting molecule. N-acetylcysteine may go through cell membranes and exert its effect inside the cells and keep the intracellular levels of glutathione high, thus reducing the active oxygen species and oxidative stress.

N-acetylcysteine reduces muscle fatigue, due to its antioxidant power and its ability to create a favorable cellular climate for muscle contraction. It also reduces muscle inflammation and speeds up recovery after intensive exercises. Protective effects of that molecule have been reported in many studies [Medved I, et al. N-acetylcysteine enhances muscle cysteine and glutathione availability and attenuates fatigue during prolonged exercise in endurance-trained individuals. J Appl Physiol 97: 1477-1485, 2004; Viña J, et al. Free radicals in exhaustive physical exercise: mechanism of production, and protection by antioxidants. Life 50: 272-277, 2000]. For an ergogenic effect, the indicated daily quantity is 20 mg/Kg/day.

Caffeine

Caffeine, although without any nutritional value, has been regarded as natural ergogenic aid as it is present in many food products sold and consumed on a daily basis [Spriet L L. Caffeine and performance. Int J Sports Nutr 5(1): 84-99, 1995]. Thus, caffeine has been used very often, particularly by athletes, as an ergogenic substance, prior to physical exercises, for the purpose of postponing fatigue and, as a consequence, improving athlete performance [Altimari L R. et al. Efeitos ergogênicos da cafeína sobre o desempenho físico. Rev Paul Educ Fis 14(2):141-58, 2000; Braga L C, ALVES M P. A cafeína como recurso ergogênico nos exercícios de endurance. Rev Bras Ciên Mov 8(3): 33-37, 2000; Sinclair C J D, Geiger J D. Caffeine use in sport: a pharmacological review. J. Sports Med Phys Fitness 40(1): 71-79, 2000].

Caffeine (1,3,7 trimethylxanthine) is a substance capable of exciting or restoring cerebral and bulbar functions, without however being regarded as a therapy drug, commonly used and freely traded, since it exhibits a low dependence induction capacity [Rang H P, Dale M M. Farmacologia. $3^{rd}$ ed. Rio de Janeiro: Guanabara Koogan, 1996].

Its action can reach all tissues, since its distribution across the organism is done by the blood stream, and it is later broken down in the form of byproducts and excreted by the urine [Clarkson P M. Nutritional ergogenic aids: caffeine. Int. J. Sports Nutr 3(1): 103-111, 1993; Spriet L L. Caffeine and performance. Int J Sports Nutr 5(1): 84-99, 1995].

Caffeine is a substance absorbed in a quick, efficient manner, by oral administration, through the gastrointestinal tract with approximately 100% bioavailability, reaching a peak of maximum concentration the blood stream following 15 to 120 minutes from ingestion [Sinclair C J D, Geiger J D. Caffeine use in sport: a pharmacological review. J. Sports Med Phys Fitness 40(1): 71-79, 2000].

The second theory assumes a direct effect of caffeine on byproducts of the skeletal muscle. The possibilities include: a change in ions, particularly sodium and potassium; inhibition of phosphodiesterase (PDE), enabling an increase in the concentration of cyclic adenosine monophosphate (AMPc); direct effect on the metabolic regulation of enzymes similar to phosphorylases (PHOS); and an increase in calcium mobilization through the sarcoplasmic reticle, which helps boost muscle contraction.

Recent studies have pointed out caffeine as a powerful agent modulating physical performance in physical activities of various natures. In this regard, the literature has been pointing out to an improvement in athlete performance in different types of physical exercise, following the intake of only 3 to 6 mg of caffeine per kilogram of body weight [Altimari L R. et al. Efeitos ergogênicos da cafeína sobre o desempenho físico. Rev Paul Educ Fis 14(2):141-58, 2000].

Backhouse and collaborators [Backhouse S H, Biddle S J, Bishop N C, Williams C. Caffeine ingestion, affect and perceived exertion during prolonged cycling. Appetite 57(1): 247-52, 2011] showed that moderate doses of caffeine consumed one hour prior to prolonged exercises induced changes in the feeling of pleasure in the exercise and that the perceived exhaustion was lower compared to the control groups.

Other research has shown an increase in muscle strength followed by higher resistance to the establishment of the muscle fatigue process following the ingestion of caffeine [Kalmar J M, Cafarelli E. Effects of caffeine on neuromuscular function. J Appl Physiol 87(2): 801-808, 1999; Lopes J M. et al. Effect of caffeine on skeletal muscle function before and after fatigue. J Appl Physiol 54(5): 1303-1305, 1983; Pinto S, Tarnopolsky M. Neuromuscular effects of caffeine in males and females. Can J Appl Physiol 22: S48, 1997; Roy B. et al. Caffeine and neuromuscular fatigue in endurance athletes. Can J Appl Physiol 19: S41, 1994].

Although it is not completely clear what mechanism of action is responsible for the muscle strength increase, it is however believed that it takes place at a higher intensity much more due to the direct action of caffeine on the central nervous system (CNS) than due to its action on a peripheral level [Kalmar J M, Cafarelli E. Effects of caffeine on neuromuscular function. J Appl Physiol 87(2): 801808, 1999].

With regard to prolonged physical exercise, the results suggest that using caffeine promotes an improvement in the metabolic efficiency of energy systems during the effort, contributing towards better physical performance [Altimari L R. et al. Efeitos ergogênicos da cafeína sobre o desempenho físico. Rev Paul Educ Fis 14(2):141-58, 2000; Braga L C, Alves M. A cafeína como recurso ergogênico nos exercícios de endurance. Rev Bras Ciên Mov 8(3): 33-37, 2000; Graham T E, Rush J W, Van Soeren M N. Caffeine and exercise: metabolism and performance. Can J Appl Physiol 19(2): 111-138, 1994; Sinclair C J D, Geiger J D. Caffeine use in sport: a pharmacological review. J Sports Med Phys Fitness 40 (1): 71-79, 2000; Spriet L L. Caffeine and performance. Int J Sports Nutr 5(1): 84-99, 1995].

Taurine

Taurine or 2-aminoethanesulfonic acid is a sulfur-containing, non-proteinogenic beta-amino acid. It is the main free amino acid in most of the tissues of mammals [Camerino D C, Tricarico D, Pierno S, Desaphy J-F, Liantonio A, Pusch M, et al. Taurine and Skeletal Muscle Disorders. Neurochem Res 29:135-42, 2004; Zhang M, Izumi I, Kagamimori S, Sokejima S, Yamagami T, Liu Z, et al. Role of taurine supplementation to prevent exercise-induced oxidative stress in healthy young men. Amino Acids 26:203-7, 2004].

The body synthesizes it through many cysteine oxidation pathways. Although taurine is synthesized mainly in the liver and brain, high levels of taurine have been found in tissues of the heart, retina, in the skeletal muscle, and in the central nervous system. There is evidence that taurine acts as a neurotransmitter (a chemical messenger for the nervous system), salt regulator, water balancer inside the cells, stabilizer of cell membranes, as well as takes part in the detoxification of foreign chemical substances and is also involved in bile production and action [Del Río H S. La taurina: esse aminoácido desconocido. Available at URL: http://www.hector.solorzano.com/articulos/taurina.html].

Another role of this amino acid is keeping the correct composition of bile and the solubility of cholesterol. Taurine binds to certain biliary salts and, for that purpose, improves its ability to digest fats. Studies with animals have demonstrated that taurine supplementation may inhibit the formation of biliary calculi [Del Río H S. La taurina: esse aminoácido desconocido. Available at URL: http://www.hector.solorzano.com/articulos/taurina.html].

Although exhibiting characteristics of an amino acid, taurine does not take part in protein synthesis, however, it is key to many biological processes, such as the development of the central nervous system and the retina, calcium modulation, membrane stabilization, reproduction, and immunity [Ripps H, Shen W. Review: taurine: a "very essential" amino acid. Molecular Vision 18: 2673-2686, 2012; Schuller-Levis G B, Park E. Taurine: New implications for an old amino acid. FEMS Microbiol Let 226(2):195-202, 2003].

In the study conducted by Silva [Silva L A, Silveira P C L, Ronsani M M, Souza P S, Scheffer D, Vieira L C, Pinho R A. Taurine supplementation decreases oxidative stress in skeletal muscle after eccentric exercise. Cell Biochem Func 29(1): 43-49, 2011], they investigated the effect of 300-mg/kg taurine supplementation on oxidative stress markers after an extenuating exercise in mice. The supplementation was conducted for 15 days. It was observed that the taurine supplementation reduced the production of superoxide radicals, lipid peroxidation, and carbonylation, evidencing the protective effect of taurine.

Another fact referred to in the literature regarding taurine is the regulation of the metabolism of carbon hydrates. According to Carneiro et al. [Carneiro E M, Latorraca M Q, Araujo E, Beltrá M, Oliveras M J, Navarro M, Martín F. Taurine supplementation modulates glucose homeostasis and islet function. J Nutr Biochem 20(7): 503-511, 2009], taurine helps control glucose homeostasis by regulating the expression of genes required to stimulate insulin secretion by β cells, increasing the peripheral sensitivity to insulin and glucose capture.

In their turn, Vettorazzi and collaborators [Vettorazzi J F, Ribeiro R A, Santos—Silva J. C, Borck P C, Batista T M, Nardelli T R, Carneiro E M. Taurine supplementation increases KATP channel protein content, improving Ca2+ handling an insulin secretion in islets from malnourished mice fed on a high-fat diet. Amino Acids 46(9): 2123-2136, 2014] supplemented taurine by 5%, during 8 weeks in mice, and verified that taurine boosted the action of insulin in the liver and the skeletal muscle of mice. Higher phosphorylation of insulin substrates was found as well as the activation of the insulin cascade, and there was consequently increased translation of glucose carriers to the cytoplasmic membrane, promoting glucose entry into the intracellular medium.

Considering the action of taurine on insulin and that this product plays an important role for athletes as it regulates the metabolism of carbon hydrates, using taurine might favor an increased availability of glucose and, as a consequence, result in higher energy production, stronger stimulation of protein synthesis and glycogen re-synthesis, in addition to possibly favoring the physical performance of athletes [Rocha, G P. Efeitos da suplementação de taurina no exercício físico. Master's Dissertation, Faculdade de Medicina da Universidade de Coimbra, 2018].

In Brazil, RDC Resolution No. 273, dated Sep. 22, 2005, from the Ministry of Health, lays down the maximum limit of taurine as an ingredient for a ready-to-consume liquid compound at 400 mg/100 mL [Brazil. RDC Resolution No. 273, dated Sep. 22, 2005, of the Health Surveillance Bureau of the Ministry of Health. Official Gazette of the Federative Republic of Brazil, Executive Branch, Brasília, DF, Sep. 22, 2005. Section 1, No. 184, p. 375-6].

Unlike the other ergogenic aids mentioned, Taurine is the first to have the advantages of using it jointly with sources of carbohydrates clearly described.

L-Carnitine

L-carnitine is a molecule already produced by the organism, specifically in the liver and kidneys, and stored in the muscles. It is synthesized in the organism from two essential amino acids: lysine and methionine, requiring the presence of vitamin C, niacin, and vitamin B6 for its synthesis. Its role is to specially help transform fat into energy [Carretelli P, Marconi C. L-carnitine supplementation in humans. The effects on physical performance. Int J Sports Med 11(1):1-14, 1990].

In addition to its primary role of burning fat by transforming it into energy, the supplement improves the ability to perform physical activities and reduces post-training pain, because it reduces the production of lactic acid, a substance that causes pain after the training. Carnitine generates a large amount of energy for the muscles, improving performance during physical exercises. That energy is taken from the fat cells.

Some studies have shown that such fat burning requires a large amount of carnitine, that's why the supplementation is recommended, always followed by physical activity. Carnitine supplementation is promising, since it improves the clinical conditions, increases tolerance to physical exercise, and, on top of that, there is evidence that it can be beneficial against cardiovascular diseases, arterial disease, kidney diseases, diabetes, and cholesterol [Coelho C F, Mota J F, Bragança E, Burini R C. Aplicações clinicas da suplementação de L-Carnitina. Ver Nutr, 18: 651-659, 2005].

Although there is not any daily intake recommendation yet, most studies with humans have used doses from 500 to 2000 mg/day of carnitine for periods of ten days to ten weeks, in addition to acute administrations, with the usually supplemented oral doses ranging from 500 to 2000 mg/day [Coelho C F, Mota J F, Bragança E, Burini R C. Aplicações clinicas da suplementação de L-Carnitina. Ver Nutr, 18: 651-659, 2005].

In a broad review regarding carnitine supplementation, Carretelli and Marconi observed that doses from 1 to 6 g/day for a maximum of six months considerably improved the plasma concentrations of carnitine, with no adverse effect or intoxication in those individuals [Carretelli P, Marconi C. L-carnitine supplementation in humans. The effects on physical performance. Int J Sports Med 11(1):1-14, 1990].

Plant-Based Proteins

The search for new food sources has aroused the interest of the scientific community concerning alternative plant-based proteins, covering traditional crops and byproducts from product processing [Ferri, P. Extração de proteínas de folhas de mandioca (*Manihot esculenta* Crants) para obtenção de concentrado protéico. 112f. Master's Dissertation, Unoeste, 2006]. Among all plant-based organic components, specifically proteins are found at high percentages in legume seeds [Richardson M. Seed storage proteins: the enzyme inhibitors. In: L. J. Rogers. Methods in plant biochemistry. London: Academic Press. Vol. 5. p. 259-305, 1991]. Globally, the plant-based proteins that are most commonly found as food products are those derived from soy or wheat [Egbert W R, Payne C T. Plant proteins. In R. Tarte (Ed.), Ingredients in meat products, properties, functionality and applications. Berlin: Springer. p. 111-131. 2009].

There is a wide range of other plant proteins that are or may be commercially available on the market, such as pea, potato, corn, canola, rice, and other proteins from legumes or oily seeds. However, most of these ingredients has some sort of use limitation, such as anti-nutritional factors and low levels of essential amino acids [Egbert W R, Payne C T. Plant proteins. In R. Tarte (Ed.), Ingredients in meat products, properties, functionality and applications. Berlin: Springer. p. 111-131. 2009; Proll J, Petzke J, Ezeagu E I, Metges C C. Low nutritional quality of unconventional tropical crop seeds in rats. J Nutrit 128: 2014-2022, 1998].

Soy Protein

Soy protein is deemed complete due to the large quantity of essential amino acids on top of many other macro nutrients with a close nutritional value than that of animal protein of high biological value [Velasquez M, Bhathenal S. Role of Dietary Soy Protein in Obesity. Int J Med Sci 4: 72-82, 2007]. Moreover, soy has a high content of proteins (38 to 42%), high concentration of BCAAs, low cost, and excellent quality, in addition to containing isoflavones. Isoflavones are a species of phytoestrogens, natural environmental substances, that is, produced by plants, with a different chemical structure than that of estrogens, but working in the same fashion. Estrogens are important in the homeostasis of the cellular and biochemical events, this fact being illustrated a wide array of illnesses caused by a deficiency in those hormones.

Phytoestrogens have gained much notoriety because they are easily found in soy, such as isoflavones [Setchell K D. Phytoestrogens: the biochemistry, physiology, and implications for human health of soy isoflavones. Am J Clin Nutrit 68, 1998]. The main isoflavones found in soy and its byproducts are daidzein, genistein, and glycitein. These compounds have antioxidant properties and perform enzyme inhibition and other processes. Over the last decades, scientific evidence has been showing that isoflavones may bring benefits to control chronic illnesses such as cancer, diabetes mellitus, osteoporosis, and cardiovascular diseases [Esteves E I, Monteiro J. Efeitos benéficos das isoflavonas de soja em doenças crônicas. Rev Nutr Camp 14: 43-52, 2001].

Supplementation with soy protein helps women lose fat mass reduce their fat percentage, and reduce their subcutaneous abdominal fat [Maesta N, Nahas E A P, Nahas-Neto J, Orsatti F L, Fernandes C E, Traiman P Burini R C. Effects of soy protein and resistance exercise on body composition and blood lipids in postmenopausal women. Maturitas 56: 350-380, 2007].

The health benefits associated with soy protein relate to physiologically active components that are part of soy, as protease inhibitors, phytosterols, saponins, and isoflavones [Potter S M. Soy—new health benefits associated with an ancient food. Nutrition Today 35, 53-60, 2000]. Other protein sources.

Other proteins that may be added for better performance of athletes from both animal and plant sources may be:
a) Proteins from lentil, pea, chickpea, quinoa, and rice:
Pea is rich in branched-chain amino acids (BCAAs) and is hypoallergenic. It contains arginine, an amino acid that helps increase immunity and fight against erectile dysfunction and improves fertility. Another compound present in the pea is lysine, which helps absorb calcium, consequentially reducing the loss of calcium in the urine and helping maintain strong bones
[https://www.mundoboaforma.com.briproteina-de-ervilha-e-boa-beneficios-e-propriedades/#PaISQgkwku3sGU3a.99],
Rice protein has good quality of amino acids, high quantities of methionine, and is deficient in lysine;
Lentil, chickpea, and quinoa proteins are high-quality products rich in amino acids and can be used as protein supplementation in vegan and/or vegetarian supplements;
b) Egg protein—albumin is a supplement with a high concentration of proteins, obtained from dehydrated and pasteurized egg white and easily digested and absorbed; its most widely known effects include an improvement of protein synthesis and reduced muscle catabolism [Alves C, Lima R V. Uso de suplementos alimentares por adolescentes. J Ped 85: 287-294, 2009]. Generally, doses of 2 to 3 g/kg of body weight are indicated. Following the training, as a whey protein replacement, albumin can be ingested jointly with some carbohydrate, which will provide the athlete with nutrients for muscle recovery and achieve higher muscle mass gains. Because it has a slow absorption, albumin is mostly indicated as a "time-release" protein, most often for periods in which the organism will not feed. In this case, it is advisable to consume the protein before bedtime [https://infinitypharma.com.br/uploads/insumos/pdf/a/albumina-po.pdf];
c) Bovine colostrum—it increases immunity and has substances to stimulate tissue development and DNA synthesis [Kishikawa Y, Wantanabe D S, Watanabe T, Kubo S. Purification and characterization of cell growth factor in bovine colostrums. J Vet Med Sci 58, 47-53, 1996].

Except for egg protein, little is known about the best composition of these protein sources as carbohydrate sources.

Phosphatidic Acids

The phosphatidic acid is a diacyl-glycerophospholipid that has been deemed to induce muscle hypertrophy through its action to activate the anabolic pathway of the mammalian target of rapamycin (mTOR) protein. The mTOR pathway works as an integrator of cellular signals and controls protein synthesis, specifically in the early process of protein translation, leading to an increase in muscle protein synthesis [Fang Y, Vilella-Bach M, Bachmann R, Flanigan A, Chen J. Phosphatidic acid-mediated mitogenic activation of mtor signaling. Science, 294(5548):1942-5, 2001].

Although few scientific data exist on the use of this supplement, the recommended 750-mg/day dose of this substance has been showing promising results [Andre T L, Gann J J, Mckinley-Barnard S K, Song J J, Willoughby D S. Eight weeks of phosphatidic acid supplementation in conjunction with resistance training does not differentially affect body composition and muscle strength in resistance-trained men. J Sports Sci Med 15(3):532-9, 2016].

Organic Extracts

The use of plant extracts containing phytochemicals that can interfere with workout performance has been described. For example, an extract of plants rich in plant steroids (e.g. *Cyanotis vaga*), green tea extract (thermogenic), an extract of algae with myostatin-inhibiting substances (*Cytoseira canariensis*—analogous to growth factor) are candidates for athlete supplementation. Other plants capable of inducing the testosterone levels (e.g. Fenugreek herb, *Tribulus terrestris*) and plants rich in flavonoids (e.g. quercetin) and triterpenes are currently being studies. Extracts with pharmacological functions may also be added to supplements such as: ginger, cinnamon, blueberry, passion fruit, pomegranate, guaco, ginseng, guarana, black tea, etc., seeking to add the supplement with their typical functional activities, such as: thermogenic, digestive, anti-inflammatory, anxiolytic, diuretic, and other properties.

Other extracts, such as extracts from propolis and its byproducts, may be used. In propolis, for instance, several phytochemicals with pharmacological effects have been described and may be suggested in athlete supplementation [Sawaya A C H F. Análise da Composição Química de Própolis Brasileira por Espectrometria de Massas. Doctor's Thesis, UNICAMP, 2006].

Steroids and Growth Factor

Hormones and steroids such as testosterone and the growth hormone work to enable muscle mass and strength gains and a body fat reduction. On the other hand, several side effects have been described and, for that reason, they have been banished by sports organizations [Kerksick C M, et al. ISSN exercise & Sport nutrition review update: research & recommendations. J Inter Soc Sport Nutr, 15:38, 2018].

Substances Currently Studied

Several substances are candidates for supplements aiming to increase physical activity performance and change the body mass. However, preliminary studies have shown that arachidonic acid, linoleic acids, aspartic acid, ferulic acid, and glycerol, although exhibiting adverse results, still need further studies to be regarded as safe candidates for athletic supplementation [Kerksick C M, et al. ISSN exercise & Sport nutrition review update: research & recommendations. J Inter Soc Sport Nutr, 15: 38, 2018].

Sodium Bicarbonate

During intensive workout, a muscle and blood buildup of acid (Hi) and carbon dioxide ($CO_2$) takes place. The bicarbonate system is the main means by which the body gets rid of acidity and $CO_2$ by converting it into bicarbonate prior to the subsequent removal from the lungs. Bicarbonate consumption (for instance, 0.3 g per kg 60 to 90 minutes before the exercise or 5 g consumed twice a day for 5 days) as sodium bicarbonate has shown to be an effective way of protecting acidity during high-intensity exercises [Kerksick C M, et al. ISSN exercise & Sport nutrition review update: research & recommendations. J Inter Soc Sport Nutr, 15: 38, 2018]. Improvements in the performance of swimmers, cyclists, and marathon athletes have been described from the use of bicarbonate [Kerksick C M, et al. ISSN exercise & Sport nutrition review update: research & recommendations. J Inter Soc Sport Nutr, 15: 38, 2018].

However, this supplement has not yet been fully tested and validated.

Fatty Acids

Fatty acids are monocarboxylic acids obtained from oils and fats. The animal organism is not capable of producing a fatty acid, thus, they can only be obtained by consuming oils and fats and exhibit important functions in the human organism, such as maintaining the levels of lipids in the blood, controlling inflammation, infections, and injuries, blood pressure, on top of favoring the production of hormones and antibodies. Fatty acids are classified according to the length of the carbon chain as well as the degree of saturation of that chain: short-chain fatty acids (with 2 to 6 carbons in each molecule); medium-chain fatty acids (6 to 12 carbons in each molecule), and long-chain fatty acids (14 to 24 carbons in each molecule). They exhibit open carbon chains that are either saturated (single bonds only) or unsaturated (one or more bonds between carbons).

Short-chain fatty acids (SOFA) are organic fatty acids containing one to six atoms of carbon. They are produced through fermentation of carbohydrates and proteins ingested in the diet, such as fibers, prebiotics, and probiotics through bacteria present in our large intestine. The growth of these bacteria is therefore beneficial to intestinal health, while at the same time inhibiting the growth of pathogenic bacteria. Thus, the diet composition directly influences the production of SCFAs. Examples of SCFAs are acetate, propionate, and butyrate.

Moreover, SCFAs are quickly absorbed and oxidized by colonocytes (colon cells) and meet approximately 60% to 70% of the energy needs of those cells. Thus, the availability of SCFAs preserves, for instance, the stocks of glutamine, which is an amino acid regarded as the primary fuel for enterocytes. Another advantage is stimulating cell proliferation in the epithelium, visceral blood flow, and increased absorption of water and sodium.

Shorter-chain fatty acids are capable of enter the mitochondria and be converted to energy through beta oxidation. Studies have shown ambiguous results as to whether these substances are ergogenic products and whether they can serve as a source of fat during workout. For example, Misell and collaborators found out that 60 g/day of an SOFA oil twice a week improved performance in athletes [Misell L M, Lagomarcino N D, Schuster V, Kern M. Chronic medium-chain triacylglycerol consumption and endurance performance in trained runners. J Sports Med Phys Fitness 41(2): 210-5, 2001]. On the other hand, Van Zyl and collaborators [Van Zyl C G, Lambert E V, Hawley J A, Noakes T D, Dennis S C. Effects of medium-chain triglyceride ingestion on fuel metabolism and cycling performance. J Appl Physiol 80(6):2217-25, 1996] reported that, while the SCFAs negatively influenced sports performance when ingested by themselves compared to the intake of carbohydrates, performance was better when the SCFAs were combined with carbohydrates. Many other studies have confirmed these results; however, the rate of gastrointestinal complaints has increased in many studies due to gastric injuries caused by these substances [Kerksick C M, et al. ISSN exercise & Sport nutrition review update: research & recommendations. J Inter Soc Sport Nutr, 15: 38, 2018]. Therefore, it is still not clear whether the SCFAs can favorably impact the acute performance in workout without scientific controversies.

Medium- and Long-Chain Fatty Acids

Medium-chain fatty acids are fats found in food such as coconut oil, palm oil, and dairy products. They are metabolized in a different manner than the long-chain triglycerides found in most other foods. Due to their shorter chain, these fatty acids are more quickly broken down and absorbed by the body. This makes them an energetic source of fat and less prone to being stored as fat. Diets rich in foods with these acids may help control cholesterol levels, however, the evidence is mixed.

Long-chain fatty acids are, for instance, oleic and linoleic acids.

The byproducts of oleic acids are the main sources of mono-unsaturated fatty acids, such as olive, canola, sunflower, soy, safflower, corn, and peanut oils, and belong to the omega 9 family. The byproducts of linoleic acids are the main sources of poly-unsaturated fatty acids and may be found in nuts, seeds, and plant oils, such as corn, sunflower, and soy, and belong to the omega 3, omega 6, and omega 9 families. Studies have shown that combined linoleic acids exhibit positive results in athletes in spite of results that still need validation [Kerksick C M, et al. ISSN exercise & Sport nutrition review update: research & recommendations. J Inter Soc Sport Nutr, 15: 38, 2018].

Oils from an animal source are also promising, such as fish oil [Pedroza A A S et al. Can fish oil supplementation and physical training improve oxidative metabolism in aged rat hearts? Life Sciences 137: 133-141, 2015].

An example of the use of that product in athletes is the oil from safflower, a plant with high oil contents (around 40%) in its seeds, especially oleic and linoleic acids, responsible for intensifying fat use by the body, making weight loss and the muscle definition easier. It is a very rich source of natural antioxidants, including the so-called tocopherols. The substances present in the safflower oil are excellent assistants for the weight loss process, help reduce cholesterol, prevent cellulites, provide energy, increase immunity, moderate the appetite, as well as help tone the muscles. The indicated consumption is two doses of 1 g each a day [Informativo técnico Dermo Ervas, Edition #42, www.dermoervas.com.br].

Calcium Pyruvate

A study assessed the effect of pyruvate in the body composition and weight of healthy women with a normal body mass index (BMI). 56 healthy women were assessed with a normal BMI (18.3 to 25.0 Kg/m2) and on a balanced diet, who would practice physical activity at least twice a week. The patients received calcium pyruvate once a day at a dose of 0.05 g/Kg/day following a saturation dose of 0.1 g/kg/day during 10 days. The total duration of pyruvate use varied from 13 to 38 days.

The measures used were weight, height, abdomen circumference, skinfolds in the triceps, abdomen, and thigh. The results indicated that 79.6% of the patients had a fat loss varying from 0.1 to 3.0 kg, with a reduction in skinfolds in 89.8% of the patients, and in 74% of them there was a reduction in the abdomen circumference. The results indicated that, in healthy women with a normal BMI, pyruvate supplementation promotes a weight reduction and diminished body fat [Fernandes C, Sbampato C G, Campomori V. Composição corporal e variação de peso em mulheres saudáveis após utilização do piruvato. Rev Bras Nutr Esport, v. 1: (3) p. 23-32, 2007].

Enzymes, Coenzymes, and Enzyme Inhibitor

It is quite well known that exhaustive exercises cause muscle damage leading to an increased concentration of enzymes in the blood plasma, such as creatine kinase, catalase, lactate-dehydrogenase, aiming to minimize the effects of reactive oxygen species. Some of that damage is due to free radicals that may cause damage on the DNA, lipids, and proteins, which may be cause of several etiologies of diseases, but can be mitigated by antioxidants. The many possible antioxidants include the use of enzymes, which has been studied and assessed.

An example is Coenzyme Q10, which is a fat-soluble vitamin similar to quinone and vital to the energy metabolism, an indispensable component of the mitochondrial respiratory chain, as well as having antioxidant activity. A double-blind, randomized study conducted by Japanese researchers aimed to examine the effects of administering coenzyme Q10 on physical fatigue. A dose of 300 mg/day of coenzyme Q10 reduced the feeling of tiredness and improved physical performance during effort tests. [Mizuno K, et al. Antifatigue effects of coenzyme Q10 during physical fatigue. Nutrition 24 (4): 293-9, 2008].

Other enzymes that are candidates for supplements are: superoxide dismutase and catalase, in addition to using allopurinol to inhibit xanthine-oxidase, showing positive effects on marathon athletes [Gomez-Cabrera M C, Domenech E, Ji L L, Viňa J. Exercise as an antioxidant: it up-regulates important enzymes for cell adaptations to exercise. Science & Sports 21: 85-89, 2006; Viňa J, et al. Free radicals in exhaustive physical exercise: mechanism of production, and protection by antioxidants. Life 50: 272-277, 2000].

The Influence of the Ingestion Time Relatively to Training and the Various Combinations of Supplements on Physical Results The muscle protein balance is higher when the availability of amino acids is increased following the exercise than when the athlete is fasting. The intracellular supply of amino acids is an determinant factor of protein synthesis, although the latter is affected by the availability of extracellular amino acids [Nissen S L, Sharp R L. Effect of dietary supplements on lean mass and strength gains with resistance exercise: a meta-analysis. J Appl Physiol 94: 651-659, 2003]. Studies have shown that whey proteins are absorbed more quickly than others, such as casein, for instance. That quick absorption causes the plasma concentrations of many amino acids, including leucine, to reach high values right after their ingestion. We can thus hypothesize that, if that ingestion were done following a workout session, the whey proteins would be more efficient in unchaining the protein synthesis process [Fischborn S C. A Influência do Tempo de Ingestão da Suplementação de Whey Protein em Relação à Atividade Fisica. Rev Bras Nutr Esport 3: 132-143, 2009]. Taking solutions containing whey proteins significantly increases the concentration of plasma insulin, which favors the capture of amino acids into the interior of the muscle cell, optimizing synthesis and reducing protein catabolism [Haraguchi F K, Abreu W C, Paula H. Proteínas do Soro do Leite: Composição, Propriedades Nutricionais, Aplicações no Esporte e Benefícios para a Saúde Humana. Rev Nutr 19: 479-488, 2006].

Such as already mentioned, Calbet and MacLean [Calbet J A L, MacLean D A. Plasma glucagon and insulin responses depend on the rate of appearance of amino acids after ingestion of different protein solutions in humans. J Nutr 132:2174-82, 2002] assessed the effect of four different solutions, one containing only 25 g/L glucose (C) and three containing 25 g/L glucose with 0.25 g/kg of body weight from three different protein sources: peas (E), whey proteins (W), and whole milk (L) on the concentrations of insulin and amino acids. They observed that, 20 minutes after ingestion, the solution containing whey proteins caused a significant elevation in the plasma concentration of insulin. There was an anabolic response to the 20 g whey protein ingestion prior to or 1 h after the workout. Besides, they asserted that the supply of amino acids, either in their free form or as proteins, combined with strength exercises, increases protein synthesis and favors the muscle protein balance.

Relatively to the moment for using the supplement, Rasmussen and collaborators [Rasmussen B B, Tipton K D, Miller S L, Wolf S E, Wolfe R R. An Oral Essential Amino Acid-Carbohydrate supplement Enhances Muscle Protein Anabolism After Resistance Exercise. J Appl Physiol 88: 386-392, 2000] demonstrated that the increase in muscle protein synthesis is similar during the supplementation with a solution of essential amino acids and carbohydrates done 1 hours after the training or 3 hours after the training. However, when that solutions was used prior to the training, the anabolic response was higher. The explanation for this phenomenon is that ingestion prior to exercise increases the flow of amino acids into the muscle [Tipton K D, Elliott T A, Cree M G, Aarsland A A, Sanford A P, Wolfe R R. Stimulation of Net Muscle Protein Synthesis by Whey Protein Ingestion Before and After Exercise. Am J Physiol Endocrinol Metab 292: 71-76, 2007].

In their turn, Esmarck and collaborators [Esmarck B, Andersen J L, Olsen S, Richter E A, Mizuno M, Kjær M. Timing of Postexercise Protein Intake is Important for Muscle Hypertrophy with Resistance Training in Elderly Humans. J Physiol 535: 301-311, 2001] investigated the importance of the ingestion time for protein supplements after strength training. Two groups of 13 men were assessed, who completed 12 weeks of training and received the same whey protein supplementation (10 grams of protein, 7 of carbohydrates, and 3 of fat) immediate after and 2 hours after the training. The group who received supplementation right after the training had an addition by 7.0% to 22.0% in their quadriceps size, whereas, in the group who received supplementation 2 hours after the training, no significant changes were detected. Similarly, muscle strength improved in the first group, but had no significant improvement in the second one. These results indicate the importance of the time at which the supplement intake must occur relatively to the physical activity.

Another study showed that the effect of supplementation on muscle anabolism is even higher if amino acids (6 g of essential amino acids plus 35 g of carbohydrates) are ingested prior to the workout [Tipton K D, Elliott T A, Cree M G, Aarsland A A, Sanford A P, Wolfe R R. Stimulation of Net Muscle Protein Synthesis by Whey Protein Ingestion Before and After Exercise. Am J Physiol Endocrinol Metab 292: 71-76, 2007]. That result is explained by Candow and collaborators [Candow D G, Burke N C, Smith-Palmer T, Burke D. G. Effect of Whey and Soy Protein Supplementation Combined with Resistance Training in Young Adults. Int J Sport Nutr Exerc Metabol 16: 233-244, 2006], leading us to believe that the time for supplement intake relatively to the training is important to create an anabolic environment that favors muscle growth.

It is scientific consensus that reduced glucose in the blood may unchain an increase in the use of the muscle glycogen reserves (glycogenolysis) during the early stages of physical exercise, negatively compromising performance, in particular prolonged efforts [Foster C. et al. Effects of pre-exercise feedings on endurance performance. Med & Sci Sport & Exerc 11(1): 1-5, 1979]. Thus, according to Coyle and collaborators [Coyle E F, et al. Substrate usage during prolonged exercise following a pre-exercise meal. J Appl Physiol 59(3): 429-433, 1985], an ingestion rich in carbohydrates prior to physical exercise must be administered around 3 hours or 4 hours before the practice so as to make the digestion process easier, normalize the glycemic and insulin levels, and ensure good energy levels.

During the physical exercise, it is important that the carbohydrate supplementation taken be quickly absorbed so that the levels of blood glucose will be maintained, especially in efforts done for prolonged periods of time, when the endogenous deposits of carbohydrates tend to reduce significantly [Mason W L, et al. Carbohydrate ingestion during exercise: liquid vs solid feedings. Med & Sci Sport & Exerc 25(8): 966-969, 1993].

Hence, a carbohydrate administration may result in increased availability of blood glucose, reducing the depletion of muscle glycogen observed in the early phases of physical performance [Ahlborg B, et al. Muscle glycogen and muscle electrolytes during prolonged physical exercise. Act Physiol Scand 70: 129-142, 1967; Coyle E F, et al. Muscle glycogen utilization during prolonged strenuous exercise when fed carbohydrate. J Appl Physiol 61(1): 165-172, 1986].

In this regard, an intake of carbohydrates every fifteen minutes during a prolonged physical effort may prevent hypoglycemia without causing an apparent change in the subjective perception of effort [Felig P, et al. Hypoglycemia during prolonged exercise in normal men. New Eng J Med 306: 895-900, 1982].

In spite of all such evidence, many studies have demonstrated that carbohydrate supplementation sharply improves physical performance only in extremely prolonged efforts (longer than two hours) [Flynn M G, et al. Influence of selected carbohydrate drinks on cycling performance and glycogen use. Med & Sci Sport & Exerc 19(1): 37-40, 1987]. The indicated supplementation in those cases should be based on glucose, sucrose, or maltodextrin, due to their quick rate of absorption.

Maltodextrin apparently causes quicker gastric emptying, in addition to lacking a sweet taste like glucose, and does not cause gastric discomfort for most people [Coggan A R, Swanson S C. Nutritional manipulations before and during endurance exercise: effects on performance. Med & Sci Sport & Exerc 24(9): S331-335, 1992]. A meal based on glucose polymers, such as maltodextrin, administered during prolonged exercises, seems to produce the necessary energy to postpone fatigue, at least in high-intensity exercises [Coggan A R, Coyle E F. Reversal of fatigue during prolonged exercise by carbohydrate infusion or ingestion. J Appl Physiol. 63(6): 2388-2395, 1987; Coyle E F, et al. Muscle glycogen utilization during prolonged strenuous exercise when fed carbohydrate. J Appl Physiol 61(1): 165-172, 1986].

In the research conducted by Andersen and collaborators [Andersen L L, et al. The effect of resistance training combined with timed ingestion of protein on muscle fiber size and muscle strength. Revista digital: Science Direct, 2005. Available at: http://linkinghub.elsevier.com/retrieve/pii/S00260495 04003063], they studied the influence of protein supplementation on long-term strength training when compared to carbohydrate supplementation. The study was conducted with 22 male individuals, at an average age of 23, during 14 weeks. The protein group received a solution containing 25 g of proteins (whey protein, casein, albumin, and glutamine), and the carbohydrate group received 25 g of maltodextrin. The vertical jump strength was analyzed in a countermovement jump with an isokinetic dynamometer, and muscle biopsy was conducted to verify the cross-sectional area of the muscle. Following the 14 weeks of strength training, higher hypertrophy was observed in the protein group than in the carbohydrate group.

The research conducted by Cribb and collaborators [Cribb P J, Williams A D, Hayes A. Creatine-protein-carbohydrate supplement enhances responses to resistance training. Med Sci Sports Exerc 39(11):1960-8, 2007] shows that the muscle hypertrophy is more efficient and significant if you combine proteins with other supplements; in that study, the group combining protein, carbohydrate, and creatine had more significant gains in the total body mass and in lean body mass than the group who only used proteins and the one who used proteins with carbohydrates.

After physical exercise, taking in carbohydrates is extremely necessary to replenish the muscle glycogen reserves depleted during the practice. In this regard, at rest, the muscle glycogen rate may be increased by using a diet rich in carbohydrates, with this procedure being recommended to enable a re-synthesis of muscle glycogen between training sessions [Liebman M, Wilkinson J G. Metabolismo dos carboidratos e condicionamento físico. In: Wolinsky, I. & Hickson Júnior, J. F. Nutrição no exercício e no esporte, p. 15-50. São Paulo: Roca, 1996].

A combination of supplements containing carbohydrates/proteins following resistance physical exercises [Zawadzki K M, et al. Carbohydrate-protein complex increases the rate of muscle glycogen storage after exercise. J Appl Physiol 72(7): 1854-1859, 1992] and strength exercises [Roy B D, Tarnopolsky M A. Influence of differing macronutrient intakes on muscle glycogen resynthesis after resistance exercise. J Appl Physiol 84(3): 890-896, 1998] seems to be more efficient for a re-synthesis of muscle glycogen than supplementation done only with carbohydrates, on top of the fact that it promotes a more significant increase in the levels of plasma insulin, and this can attenuate protein breakdown and/or increase protein synthesis.

The state-of-the-art conclusion indicates that most studies have shown that using food supplements in different combinations is beneficial to muscle growth and protection in individuals engaged in physical activity, in a quicker, more efficient manner than using such resources individually or not using them. Although the results are varied, there is a direction in the works clearly pointing out that supplementation is a fundamental strategy for strength gains and maintaining muscle integrity.

Vitamin and Mineral Supplementation

From a physiological standpoint, vitamin supplementation is only defended when used to treat some existing nutritional deficiency or further to reach the recommended quantities beyond food consumption. In spite of the high energy need of individuals engaged in physical exercise, higher vitamin requirements may be met by consuming a varied and balanced diet. On the other hand, Kleiner and Greenwood-Robinson as well as Krause and Tirapegui [Kleiner S M, Greenwood-Robinson M. Nutrição para o treinamento de força. 1$^{st}$ ed., São Paulo: Manole, 2002. 239 p; Krause. Alimentos, nutrição e dietoterapia. Edited by L. Kathleen Mahan, Sylvia Escott Stump; 11$^{th}$ ed., São Paulo: Roca, 2005. 1242 pg.; Tirapegui, J. Nutrição, metabolismo e suplementação na atividade física. São Paulo: Atheneu, 2005. 300 pg] asserted that a vitamin and mineral intake requires attention, with regard to the consumption of antioxidant vitamins and minerals, since they take part in neutralizing the free radicals through both aerobic and anaerobic activity. According to the same authors, cell structures are destroyed by free radicals, and vitamins C, E, and β-carotene and minerals, such as selenium, zinc, copper, and magnesium, can protect these cell structures.

Minerals are essential inorganic elements for metabolic processes and serve as a cell structure, enzymatic and hormonal components, and on top of acting as regulators of the metabolic and neuronal control. In athletes, changes in the sodium, potassium, and magnesium levels are considerable in moderate to high exercise intensities and, in these situations, these athletes must take in these minerals seeking to avoid a mineral imbalance in the body [Kerksick C M, et al. ISSN exercise & Sport nutrition review update: research & recommendations. J Inter Soc Sport Nutr, 15: 38, 2018].

Tirapegui [Tirapegui, J. Nutrição, metabolismo e suplementação na atividade física. São Paulo: Atheneu, 2005. 300 pg] stresses that, when planning a diet for a person engaged in physical activity, an increase in the daily energy expenditure and, as a result, supplementation in training and physical exercises should be considered.

Generally, there are important differences between the supplementation needs of men and women. In general, women need to consume more iron than men do to compensate for the blood lost during menstruation. The complicated part is that women eat less than men, but need iron as much as they do. Secondly, heavy workout increases the iron requisites as it increases the iron losses in the body especially through sweating. With a recommended daily iron consumption of 18 mg/day for women and 8 mg/day for men, iron can increase aerobic performance, since it is a component of blood hemoglobins, in charge of carrying oxygen through the body [Kerksick C M, et al. ISSN exercise & Sport nutrition review update: research & recommendations. J Inter Soc Sport Nutr, 15: 38, 2018].

Sodium is the most important electrolyte found in the cells of the body, while potassium is its "counterweight" inside the cells. It is essential for the absorption of nutrients during digestion. Glucose and amino acids are actively carried into most of the cells against a large concentration gradient. Indirectly, sodium also contributes toward the maintenance of the acid-base balance, which is key to the good functioning of cells. Besides, sodium helps conduct nervous impulses and control muscle contraction. A sodium concentration helps regulate the blood pressure and distribute fluids and nutrients inside and outside the cells.

When the sodium concentration is abnormal, a delicate balance is disturbed and the body functions are jeopardized. Fortunately, the body has a very complex system involving kidneys and thirst to regulate the amount of sodium and water taken in, as well as the quantity of these and other electrolytes (potassium, chloride, etc.) that are excreted in the urine. Electrolytes, in particular sodium, are also lost in other body fluids, especially sweat. Massive losses of sweat may potentially deplete the electrolyte reserves in the body and, for that reason, they must be replenished in athletes [Burke L, Cox G. The Complete Guide to Food Sports Performance. A Guide to Peak Nutrition For Your Sport. 3$^{rd}$ Edition. Ed. Allen & Unwin: Crows Nest, Australia].

For men and women, the recommended sodium intake according to the World Health Organization is 2.0 g/day [https://www.minhavida.com.br/alimentacao/galerias/16038-oms-divulga-novas-orientacoes-no-consumo-de-sal-e-potassio-para-adultos-e-criancas].

Important minerals that can affect physical activity:

Calcium: important to maintain the bone composition balance;

Magnesium: activates enzymes involved in protein synthesis and may be involved in ATP metabolism. Moreover, magnesium chelates such as magnesium glycyl-glutamine and magnesium bis-creatine are capable of promoting muscle anabolism on levels comparable to the anabolic steroid testosterone, with the advantage that they do not produce side effects [Informativo técnico Dermo Ervas, Edition #42, www.dermoervas.com.br];

Phosphorus: improves the transportation of cell oxygen;

Potassium: helps with the acid-base and electrolytical balance of cells;

Selenium: antioxidant with a synergetic activity with vitamin E;

Copper: important enzymatic cofactor involved in the formation of blood cells and melanin;

Molybdenum: important in iron metabolism;

Zinc: important enzymatic cofactor. Studies have indicated that a 25-mg/day supplementation of that mineral during physical training minimized changes in the immune system [Kerksick C M, et al. ISSN exercise & Sport nutrition review update: research & recommendations. J Inter Soc Sport Nutr, 15: 38, 2018];

Sodium phosphate: cell structure element, this mineral has been shown to improve oxygen transportation and modulate other reactions. Supplementation with this mineral has been showing an improvement of the aerobic activity [Kerksick C M, et al. ISSN exercise & Sport nutrition review update: research & recommendations. J Inter Soc Sport Nutr, 15: 38, 2018].

On the other hand, minerals such as boron, chromium, and vanadium have not exhibited so far any relationship to physical performance and are not recommended as supplement components.

In the case of vitamins, several studies have shown that their addition has not improved physical performance in athletes, however, they may be directly associated with muscle protection. In general, muscle pains following physical training are responses to an injury to tissues and, in these situations, several proteins are secreted to fight reactive oxygen species in charge of inflammation processes and contusions, which can be inactivated by vitamins [Cruzat V F, et al. Current aspects about oxidative stress, physical exercise and supplementation. Ver Bras Med Esporte 13: 304-310, 2007].

Vitamins are involved in many reactions including the production of blood cells, antioxidant actions, tissue repair, and protein synthesis. When the vitamin levels in the body drop, there may be indirect changes that may affect the physical activity of athletes. Therefore, in spite of little scientific evidence in physical performance correlating to vitamins, its role is key to body balance.

For instance, vitamins C and E are capable of reacting to reactive oxygen species and other radicals and, thus, have been tested in athlete supplementation by assessing their influence on fighting oxidative muscle stress. Positive results were shown in the survey conducted by Cruzat and collaborators, showing that the 1000 UI/day supplementation of vitamin E reduced the concentration of a protein associated with muscle injury in the blood plasma. In the case of vitamin C, a 400-mg/day dose increased the tissue concentration of the vitamin, which can be released into the blood circulation during the workout [Cruzat V F, et al. Current aspects about oxidative stress, physical exercise and supplementation. Ver Bras Med Esporte 13: 304-310, 2007]. Moreover, the iron in the meal or supplement is better absorbed if vitamin C is present.

Thus, although vitamins are not energy sources for the body, maintaining their levels can help with the overall balance of the body before, during, and after exercises and indirectly act as essential supplements; therefore, they can be added in formulas for athletes.

Form of Supply of the Supplement and Swallowing

The supplement/energetic food proposed here can be supplied in different forms: a) Liquid form; b) Gel form; and c) Paste form. The difference consistencies are forms of supplying the product and each of them has a role, as well as are a different form of consumption with regard to its deglutition and swallowing.

Overall, the control over the gastrointestinal functions, in response to a consumed food, is regulated by an intricate pathway of neural reflexes. For instance, the presence of food in the mouth starts a mechanical and chemical neural stimulus that leads to increased salivary secretion in the oral cavity. [Pedersen, et al. Saliva and gastrointestinal functions of taste, mastication, swallowing and digestion. Oral Diseases, 8: 117, 129, 2002].

The primary roles of the oral phase are to mechanically break the food into small particles through mastication and added saliva carrying several enzymes, which strengthens the taste of the food, as well as helps the digestion of starch and lipids and the formation of the bolus to be swallowed [Nauntofte B, Jensen J L. Salivary secretion. In: Yamada T, Alpers D N, Laine L, Owyang C, Powell D W, eds. Textbook of Gastroenterology, $3^{rd}$ edn. Lippencott Williams, Wilkins Publishers: Philadelphia, pp. 263-278, 1999].

The swallowing process is in short divided into three phases: 1°) oral phase of bolus formation in the oral cavity; 2) involuntary phase of the pharynx, which carries the bolus by peristaltic movements, and 3) involuntary phase that entails an esophagus contraction and directs the bolus down to the stomach. There is an intricate system of brain modulation and signaling and nerve control that enables perfect deglutition [Pedersen, et al. Saliva and gastrointestinal functions of taste, mastication, swallowing and digestion. Oral Diseases, 8: 117, 129, 2002; Thexton A J Mastication and swallowing: an overview. Br Dent J 173:197-206, 1992].

In healthy individuals, the frequency of swallowing is in average 600 times in 24 hours, with salivary production ranging from 0.5 to 1.5 L of saliva [Pedersen, et al. Saliva and gastrointestinal functions of taste, mastication, swallowing and digestion. Oral Diseases, 8: 117, 129, 2002].

From that perspective, the product in liquid or paste form, upon entering the oral cavity, stimulates saliva formation to make swallowing easier and requires an intensive saliva flow until all the food is completely swallowed. In that case, the liquid or paste comes into contact with all oral cavity tissues, including the teeth.

In its gel form, the product is added in small blocks and, upon entering the oral cavity, requires a lower salivary production, as it is intended for the consumer of this type of product not to chew it and swallow it whole. Thus, athletes engaged in intense and/or various physical activities, when consuming the supplement in gel form, may reduce and/or avoid taking in liquids to help with swallowing, as well as there is a reduced sensation of thirst. Moreover, in gel form, there is a reduced time of residence in the oral cavity and, as a consequence, shorter contact with the teeth, thus possibly reducing the possibility of a cariogenic biofilm and dental diseases when compared to the liquid or paste form of the product.

It is in this scenario that the state of the art presented is considered, with nutritional supplements for sports applications in general. Nonetheless, considering the above, we can notice that there is still no consensus about the best food composition to combine ergogenic effects and an optimal source of carbohydrates to achieve the best metabolic results focused on workout and physical activities of various types.

Many studies and products called "energetic" available on the market focus on carbohydrates originating in corn, such as maltodextrin or dextrose.

But there is a lack of studies assessing the adequacy of enzymatically inverted brown sugars derived from the sugarcane for that function.

It would therefore be important to develop different types of food supplements focused on sports and physical activities, containing inverted sugars originating in the sugarcane and different ergogenic products, reaching a high-performance, high-energy-power composition that could be used by professional and amateur athletes at different times, before, during, and after the workout, regardless of sex and age.

SUMMARY OF THE INVENTION

This invention therefore lays out the production process and the composition, as thus obtained, of an energy supplement/foodstuff product derived from brown sugars, originating in the sugarcane, exhibiting in a single product advantages in exercise response due to its equimolar composition of glucose and fructose and sensorial qualities superior to the "energy products" described in the state of the art coming from a combination of several sources of carbohydrates and the fact that no added conservatives are needed. This invention reports different forms of obtaining optimal compositions for a combination of this source of carbohydrates and ergogenic products, as well as being rich in vitamins, essential minerals, whether by adding these elements or because they are already originally present in the sugars used as a source of carbohydrates.

All of this is in addition to the fact that it has its natural sweetness derived from the sucrose inversion into glucose and fructose, leading to a taste deemed superior to energy products based on corn carbohydrates, in the opinion of athletes in surveys conducted for this invention.

In its first modality, this invention has a composition or supplement/foodstuff of high energy power that fulfills the needs for sources of healthy carbohydrates of both athletes and non-athletes, supplying not only energy but also vitamins, added with essential minerals and ergogenic products, such as proteins (whey protein and soy protein), caffeine and maltodextrin, and others described in the state of the art.

On top of that, it has an ability to generate effectiveness gains in physical activities at various stages of the exercises: low-intensity, medium-intensity, and high-impact exercises, since each of them requires a certain availability of energy in the form of carbohydrates. All of them can be fulfilled by these compositions.

More specifically, the compositions may take the form of a gel, which is appropriate in cases of use during the workout, when compared to liquid energy products. This gel is rich in carbohydrates, primarily coming from sugarcane sucrose, inverted into glucose and fructose preferably through enzymes, such as using the invertase enzyme, but which can also be obtained through chemical inversion and/or from resins. Moreover, the sugars can be organic and already naturally rich in minerals and pharmacologically active substances, making this supplement/foodstuff nutraceutical.

This product, with all of the above-described attributes, can perfectly be regarded as a vegan and/or organic product, as it is manufactured based on plants, and can therefore be sold with this commercial appeal, provided that its additives are not from an animal source.

Thus, the compositions presented here bring advantages when compared to commercial products as described in the state of the art, especially when compared to those using carbohydrates poor in minerals and vitamins, generally coming from corn starch.

In the second modality of this invention, the different production processes for the abovementioned food compositions are presented.

DETAILED DESCRIPTION OF THE INVENTION

This invention therefore describes a HIGH-ENERGY FOOD SUPPLEMENT BASED ON INVERTED SUGARS AND ERGOGENIC PRODUCTS FOR USE IN PHYSICAL ACTIVITY AND THE METHOD FOR THE SAME, seeking to fulfill the demands of those engaged in moderate-to high-performance workout and physical activity.

The SUPPLEMENT/FOODSTUFF IN LIQUID OR GEL FORM of this invention is formulated from a syrup rich in carbohydrates originating in the sugarcane and inverted preferably by enzymatic means, which replaces, with many advantages, starch-based carbohydrates present in the energy products available on the market and described in the state of the art, due to the fact that its composition primarily includes glucose and fructose on an equimolar basis.

In the enzymatic inversion process, the inversion rate can reach 98% and, in that situation, sucrose is converted into equimolar parts of glucose and fructose, without losing any nutritional characteristic in terms of vitamins, antioxidants, and minerals present prior to inversion. Because it preferably uses a biological catalyst, the invertase enzyme (GMO-free), this process does not form toxic compounds, such as the ones observed in chemical inversion and/or resin-based inversion, and preserves the primary product characteristics. On top of that, this syrup, with equimolar quantities of glucose and fructose and a low sucrose concentration, enables immediate metabolization by the athlete, giving them energy and muscle protection when they need it most in the physical activity.

It can be further stressed that, with the enzymatic inversion process, the sweetness of conventional sugar is boosted and can be raised to 100 and even 120, with a 20% gain relatively to sucrose. This provides a naturally tasteful and healthy supplement/foodstuff.

It is worth highlighting that, in 100 grams of brown sugars, such as VHP or demerara, several minerals are present. Their mineral composition directly depends on the type of directly depends on the type of sugarcane cultivar, the agricultural treatment, crop region, and others. However, several studies show that, the darker and, obviously, the less "treated" a sugar product is, the more minerals will be conserved in it, as shown by Silva in Table 1 [SILVA, A. F. S. Caracterização e determinação de minerais em amostras de açúcares brasileiros. Master's Thesis. ESALQ, USP, Piracicaba, 2017]. Vitamins B1, B2, and B6 and antioxidants are also present.

TABLE 1

Range ofv concentration obtained for minerals analyzed by ICP OES in the various types of sugar. ICP-OES: Inductively Coupled Plasma Optical Emission Spectrometry.

| Element | Refined (mg kg$^{-1}$) | Coarse (mg kg$^{-1}$) | Demerara (mg kg$^{-1}$) | Brown (mg kg$^{-1}$) |
|---|---|---|---|---|
| Mn | 0.005 to 0.30 | 0.03 to 0.4 | 0.2 to 1.5 | 4.4 to 25.8 |
| Mg | 0.6 to 15.7 | 2.6 to 32.5 | 12 to 79 | 175.8 to 1065.5 |
| K | 0.45 to 69.5 | 4.7 to 81 | 14 to 49 | 439.8 to 2891.5 |
| S | 5 to 37 | 16 to 102 | 41.4 to 163.7 | 56.3 to 1154.5 |
| P | 0.1 to 9 | 1.5 to 9 | 4.5 to 20.2 | 30 to 338.1 |
| Zn | 0.07 to 0.5 | 0.07 to 1 | 0.09 to 0.36 | 1.05 to 5.6 |
| Ca | 4 to 101.5 | 106 to 1214 | 80.2 to 244.2 | 275 to 2346 |
| Cu | 0.005 to 0.230 | 0.01 to 0.30 | 0.06 to 0.2 | 0.3 to 1.7 |
| Fe | 1.7 to 17.5 | 0.8 to 9 | 3.3 to 57.8 | 23.5 to 298.2 |
| Si | 7.5 to 32 | 10 to 27 | 11.4 to 65.4 | 50 to 2808 |

Pharmacological compounds are present in the VHP, Demerara, and Brown sugars, such as flavonoids and phenolic acids, such as luteolin, apigenin, tricine, quercetin, kaempferol, caffeic acid, apigenin, luteolin, tricine, chlorogenic acid, coumaric acid, and ferulic acid. These compounds are directly associated with several pharmacological activities such as antioxidant, anti-inflammatory, antimicrobial, and even anti-tumor properties [Valli V, Gomez-Caravaca A. M.; D I Nunzio M., Danesi F, Caboni M F, Bordoni A. Sugar cane and sugar beet molasses, antioxidant-rich alternatives to refined sugar. J. Agri Food Chem, 2012, 60, 12508-12515; Alves V. G, Souza A G, Chiavelli L U R, Ruiz A L T G, Carvalho J E, Pomini A M, Silva C C. Phenolic compounds and anticancer activity of commercial sugarcane cultivated in Brazil. Na. Acad. Bras, Cienc. 2016, 88, 1201-1209; Taylor R P. Discovery of bioactive natural products from sugarcane. Master of Science Thesis. School of Environmental Science and Management, Southern Cross University, Lismore N S W, Australia. 2018; Almeida J M D. Flavonóides e ácidos cinâmicos de cana-de-açúcar (*Saccharum officinarum* L.—Poaceae) e seus produtos. Identificação e atividade antioxidante e antiproliferativa. Doctor's Thesis. University of São Paulo, 2006]. Studies have shown that dark sugars help maintain the muscle tone of the digestive tract wall; improve the health of the nervous system; strengthen the skin, nails, and hair; improve the functioning of the liver, speed up the healing of injuries, and prevent and treat anemia due to the iron present.

Therefore, this is a composition with unexpected effects, both in sensorial terms among "energy products" and carbohydrate concentration and in the nutritional and functional appeal far superior to the attributes of other energy gels described in the state of the art.

To better illustrate this assertion, Table 2 presents the market-leading products (2019), in this field of work. Compared to the supplement/foodstuff of this invention, which will henceforth be called Carbo Bio Gel or only Carbo Bio. They are: GU, Carb UP, Aoo, VO2 Energy Gel, Hammer Gel, and Exceed Energy Gel. The formulation basis of those products are carbohydrates coming from starch digestion sugars: dextrose and maltodextrin, usually from corn, which are poor in minerals and vitamins. Some are artificially enriched with proteins and vitamins. However, all of them have chemical conservatives in their formulas.

TABLE 2

Nutritional comparison between the various energy products with respect to the various formulations of the base gel of this invention (Carbo Bio Gel) produced based on the VHP/Demerara sugar.

| Product 30-g Portions | Carbo Bio Gel | GU | Carb UP Black | Aoo | VO2 Energy Gel | Hammer Gel | Exceed Energy Gel |
|---|---|---|---|---|---|---|---|
| Carbohydrate (%) | 82.0 | 68.7 | 60.0 | 68.7 | 63.3 | 63.3 | 70.0 |
| Calories (Kcal) | 97.8 | 100.0 | 72.0 | 82.5 | 72.0 | 81.8 | 84.0 |
| Amino acids | + | + | 0 | 0 | 0 | + | 0 |
| Sodium (mg) | 63.0 | 56.2 | 0 | 46.9 | 58.0 to 62.0 | 22.7 | 82.0 |
| Dextrose (starch) | 0 | 0 | + | + | + | + | + |
| Fructose | + | + | + | + | + | + | 0 |
| Cane glucose | + | 0 | 0 | 0 | 0 | 0 | 0 |
| Maltodextrin | + | + | + | + | + | + | + |
| Gel | + | − | − | − | − | − | − |
| Fats | 0 | 0 | 0 | 0 | 0 | 0 | 0 |
| Proteins (%) | + | 0 | 0 | 0 | 0 to 3.3 | 0 | 0 |
| Vitamin B | + | 0 | + | 0 | 0 | 0 | 0 |
| Corn starch | 0 | 0 | + | 0 | 0 | 0 | 0 |
| Chemical conservatives | 0 | + | + | + | + | + | + |
| Caffeine (mg) | 81 | 0 | 81 | 0 | + | 0 | 0 |
| Minerals | + | + | + | 0 | + | + | 0 |
| Whey Protein | + | 0 | 0 | 0 | + | 0 | 0 |
| Vitamin C (mg) | + | 0 | 0 | 0 | 22.0 | 0 | 14.0 |
| Vitamin E (mg) | + | 0 | 0 | 0 | 4.6 | 0 | 30 |
| Apple juice syrup | + | 0 | 0 | 0 | 0 | + | 0 |

The need for chemical conservatives in these commercial energy products is due to the fact that the dextrose concentration is not higher than 70% in the syrups, since, if it is more concentrated, dextrose precipitates and the materials becomes hardened and crystallized. On the other hand, the sugar proposed here, coming from cane sucrose, can be produced with high concentrations, above 80%, which greatly limits the proliferation of microbial contaminants due to the osmotic pressure and, as a consequence, chemical conservatives are not needed.

In addition to the above-mentioned advantages, the possibility of a higher concentration of carbohydrates in the gel syrup of this invention (Carbo Bio Gel) enables the formulation of more powerful energy gels and the possibility of several formulations to offer the client a healthier, more natural product when compared to the similar products presented before.

In a controlled study, conducted in a laboratory for sensorial analysis purposes, one of the formulations of this invention, without additives, was tested in 7 different amateur athletes, who engage in 3 different fields of sport: soccer, tennis, and marathon.

This study will be described below in a summarized manner only to illustrate the sensorial potential of the formulations of this invention, through the opinion of those different athletes. In the study, we had the following answers:

All voluntary athletes in the study asserted that they use energy gels in their activities. Concerning their frequency of use, the athletes claimed that: 42.9% use energy gels twice to three times a week; 28.6% use at least once a week; 28.6% do not use them frequently, and none of them use them more than three times a week.

In a first approach after they tried Carbo Bio Gel, they were asked "Would you replace your frequently used product with Carbo Bio Gel?":

71.4% of the athletes answered that they would;
14.3% answered that they could not tell;
14.3% answered that it would not be applicable, since they do not use it frequently enough to answer the question properly.

Moreover, 100% of the interviewed athletes asserted that Carbo Bio Gel played the role of a supplement/energy food and thus optimized their performance through the exercise.

Specifically as to the taste:

71.4% of the athletes claimed that it tastes better than commercial gels, whereas 28.6% said that it tastes the same. There was no claim that the product is worse.

The athletes were also inquired about whether they would consider to be "very important" the following question concerning one of the characteristics of Carbo Bio Gel: "Carbo Bio Gel has as one of its characteristics/benefits the fact that it has a higher percentage of carbohydrates per weight than its commercially available competitors, and this enables the intake of a reduced quantity of gel to obtain the same energy value. How important is that to you?":

100% of the athletes regarded this as "very important".

This study could assess the satisfaction level regarding the product by assessing how they would recommend Carbo Bio Gel to other athletes, using a Net Promoter Score (NPS) question, "In a scale from 0-10, how much would you recommend Carbo Bio Gel to a friend or colleague?":

One (01) athlete answered 8 and was rated as a neutral consumer;
Six (06) athletes answered between 9 and 10 and were rated as promoter consumers with respect to Carbo Bio Gel.

As the answers were very positive, we can determine that the basic composition of Carbo Bio Gel, even without additives, already exhibits sensorial characteristics and effectiveness in physical activity, even high-performance workout, equivalent to and/or better than those of other products available on the market (so far).

This invention additionally provides an increment to the tested composition for the purpose of making it even more effective, however maintaining its taste. The above-tested composition can be improved with some ergogenic additives, which may be added to the product to increment the energy power of Carbo Bio Gel.

The ergogenic products that can be used as additives in the gel composition of this invention include, as an example, maltodextrin, caffeine, guarana, proteins and amino acids in general (whey protein and fractions, BCAAs, and plant-based proteins), and others that are presented and detailed in the state of the art as described in the backgrounds of this invention. Preferably, maltodextrins based on a non-GMO (Genetically Modified Organism) raw material, such as potato, cassava, etc., avoiding, without limitation, the use of materials coming from GMO corn.

On a non-exhaustive basis, we have the following ergogenic products and additives that can be used in the compositions of this invention: BCAAs, isolated leucine and byproducts, whey protein, creatine, glutamine and byproducts, arginine, alanine, caffeine, taurine, carnitine, plant-based proteins (e.g. soy, lentils, peas, chickpeas, quinoa, and rice), plant extracts, phosphatidic acid, sodium bicarbonate, minerals, vitamins, egg proteins, bovine colostrum, maltodextrins, palatinose, erythritol, maltose, mannitol, mannose, sorbitol, cyclodextrins, fructooligosaccharides, fatty acids, cellobiose, trehalose, chitin, chitosan, and other examples of carbohydrates and nutritional, pharmacological, and physiological ergogenic products and/or additives described in the state of the art, at a use validation stage, or yet to be launched into the market.

As to the form of supply, the product can be in liquid, paste, or gel form. Each of these consistencies is consumed in a different way, depending on the athlete's interests, as described in the state of the art.

The various formulations, regarded as optimal for this invention, are presented in the following examples, in which the end composition has once again been called Carbo Bio Gel to distinguish it from the compositions previously found in the state of the art and on the market. Thus, the examples of the Carbo Bio Gel composition are:

Example 1—Carbo Bio Gel Production from Coarse Sugarcane Sugar Inverted Enzymatically 1. Solid sucrose is diluted with water to a sucrose syrup at 78.0° Brix and heated at 80° C. for total dissolution of the sugar, through agitation in the tank;
2. The syrup is cooled down to 55.0° C., and the pH adjusted at 4.5 using citric acid. In that syrup, the invertase enzyme (whether or not GMO-free) is added as indicated for commercial applications, and the reaction is kept for the time required to ensure the necessary inversion percentage; After the invention, the syrup reaches 80° Brix naturally due to the heating;
3. The syrup is filtered for removal of particulates;
4. The filtered syrup can be added with maltodextrin in a proportion of 0.5% to 33.0% (w/w), preferably at a 33.0% (w/w) concentration of maltodextrin, seeking a composition balance in which the end product exhibits 2 parts of glucose and 1 part of fructose, since in that concentration balance there is scientific evidence of increased physical performance [Currell K, Jeukendrup A E. Superior Endurance Performance with Ingestion of Multiple Transportable Carbohydrates. Med & Sci Sport & Exerc. DOI: 10.1249/mss.0b013e31815adf19].

Thus, EXAMPLE 1 refers to:

using COARSE SUGAR (organic, non-organic, or refined) as the basis for the Carbo Bio Gel product of this invention;

ENZYMATICALLY inverted at different rates of inversion (sucrose:glucose:fructose ratio preferably with an inversion of sucrose at 90% to 98% (w/w));

added with MALTODEXTRIN (from corn, cassava, or sweet potato, either GMO-free or conventional).

TABLE 3

Example of Carbo Bio Gel composition based on enzymatically inverted coarse sugar and its natural minerals.

| Components | Carbo Bio Gel Coarse Sugar |
|---|---|
| Water (%) | 15.0-20.0 |
| Fructose (%) | 30.0-45.0 |
| Glucose (%) | 24.0-40.0 |
| Sucrose (%) | 0.1-4.8 |
| Maltodextrin (%) | 0.5-33.0 |
| Amino Acids and Proteins (mg/100 g) | 0.2-0.4 |
| Sodium (mg/100 g) | 1.6-17.0 |
| Zinc (mg/100 g) | 0.007-0.1 |
| Potassium (mg/100 g) | 0.47-8.1 |
| Magnesium (mg/100 g) | 0.26-3.25 |
| Calcium (mg/100 g) | 10.6-121.4 |
| Iron (mg/100 g) | 0.08-0.9 |

Example 2—Carbo Bio Gel Production from Coarse Sugarcane Sugar Inverted Chemically 1. Solid sucrose is diluted with water to a sucrose syrup at 78.0° Brix and heated at 80° C. for total dissolution of the sugar, through intensive agitation in the tank; Phosphoric acid is added to the syrup up to pH 2.0 to 2.5, keeping it at 95° C. until the desired inversion rate;
2. The syrup pH is corrected with soda ash to pH 4.5 to 5.0;
3. The syrup is filtered for removal of particulates;
4. The filtered syrup can be added with maltodextrin as shown in example 1.

Thus, EXAMPLE 2 refers to:

using COARSE SUGAR (organic, non-organic, or refined) as the basis for the Carbo Bio Gel product, as shown in example 1, however not using an enzyme;

CHEMICALLY inverted at different rates of inversion (sucrose:glucose:fructose ratio preferably with an inversion of sucrose at 90% to 98% (w/w));

added with MALTODEXTRIN (from corn, cassava, or sweet potato, either GMO-free or conventional).

TABLE 4

Example of Carbo Bio Gel composition based on chemically inverted coarse sugar and its natural minerals.

| Components | Carbo Bio Gel Sugar Coarse |
|---|---|
| Water (%) | 15.0-20.0 |
| Fructose (%) | 30.0-45.0 |
| Glucose (%) | 24.0-40.0 |
| Sucrose (%) | 0.1-4.8 |
| Maltodextrin (%) | 0.5-33.0 |
| Amino Acids and Proteins (mg/100 g) | 0.2-0.4 |
| Sodium (mg/100 g) | 1.6-17.0 |
| Zinc (mg/100 g) | 0.007-0.1 |
| Potassium (mg/100 g) | 0.47-8.1 |
| Magnesium (mg/100 g) | 0.26-3.25 |
| Calcium (mg/100 g) | 10.6-121.4 |
| Iron (mg/100 g) | 0.08-0.9 |

It is worth stressing that, with a sucrose inversion using the traditional chemical method, the initial syrup has a maximum concentration of 60° Brix due to the need for filtrations to remove color and odor, and, after the inversion, the syrup pH needs to be corrected using soda ash, a fact that saturates the syrup with undesirable sulfates, and then the syrup is filtered and concentrated on evaporators, which further reduces its quality due to the additional build-up of undesirable substances such as: furfural, hydromethylfurfural, and mainly sulfooxymethylfurfural, given its capacity to react to the DNA and cause mutations [Ogando F I B. Estudo da degradação térmica de sacarose e da contaminação microbiológica no processo de fabricação de açúcar. Master's Theses, ESALQ/USP, 2015].

Example 3—Carbo Bio Gel Production from Coarse Sugarcane Sugar Inverted Chemically Following the Positive List of Organics 1. Solid sucrose is diluted with water to a sucrose syrup at 78.0° Brix and heated at 80° C. for total dissolution of the sugar, through intensive agitation in the tank;
2. Acid is added to the syrup up to pH 2.0 to 2.5, keeping it at 95° C. until the desired inversion rate. The acid is used in this process must be allowed on the Positive List of Organics (executive instruction No. 18, dated May 28, 2009, Law 10831, dated Dec. 23, 2003); example: citric acid;
3. The syrup pH is corrected with products allowed on the Positive List of Organics (executive instruction No. 18, dated May 28, 2009, Law 10831, dated Dec. 23, 2003); to pH 4.5 to 5.0;
4. The syrup is filtered for removal of particulates;
5. The filtered syrup can be added with an additive as shown in example 1.

Thus, EXAMPLE 3 refers to:
using ORGANIC COARSE SUGAR as the basis for the Carbo Bio Gel product, as shown in example 2, however using the positive list of chemicals;
CHEMICALLY inverted with products allowed on the Positive List of Organics at different inversion rates (sucrose:glucose:fructose ratio preferably with an inversion of sucrose at 90% to 98% (w/w)), thus regarded as an organic syrup;
added with MALTODEXTRIN (from corn, cassava, or sweet potato, either GMO-free or conventional).

TABLE 5

Example of Carbo Bio Gel composition based on chemically inverted coarse sugar following the Positive Organic List and its natural minerals.

| Components | Carbo Bio Gel Coarse Sugar |
|---|---|
| Water (%) | 15.0-20.0 |
| Fructose (%) | 30.0-45.0 |
| Glucose (%) | 24.0-40.0 |
| Sucrose (%) | 0.1-4.8 |
| Maltodextrin (%) | 0.5-33.0 |
| Amino Acids and Proteins (mg/100 g) | 0.2-0.4 |
| Sodium (mg/100 g) | 1.6-17.0 |
| Zinc (mg/100 g) | 0.007-0.1 |
| Potassium (mg/100 g) | 0.47-8.1 |
| Magnesium (mg/100 g) | 0.26-3.25 |
| Calcium (mg/100 g) | 10.6-121.4 |
| Iron (mg/100 g) | 0.08-0.9 |

Example 4—Carbo Bio Gel Production from Coarse Sugarcane Sugar Inverted Using Commercially Available Resins 1. Solid sucrose is diluted with water to a sucrose syrup at a maximum of 60.0° Brix and heated at 70° C. for total dissolution of the sugar, through intensive agitation in the tank;
2. The diluted syrup is pumped into columns containing synthetic resins to remove color and salts. Then, the syrup passes through commercially available synthetic resins that break the sucrose molecule into glucose and fructose;
3. The inverted syrup is concentrated for instance on evaporators up to 80° Brix and filtered for removal of particulates;
4. The filtered syrup can be added with maltodextrin as shown in example 1.

Thus, EXAMPLE 4 refers to:
using COARSE SUGAR (organic, non-organic, or refined) as the basis for the Carbo Bio Gel product;
inverted USING RESINS at different rates of inversion (sucrose:glucose:fructose ratio preferably with an inversion of sucrose at 90% to 98% (w/w));
added with MALTODEXTRIN (from corn, cassava, or sweet potato, either GMO-free or conventional).

TABLE 6

Example of Carbo Bio Gel composition based on coarse sugar inverted using resins.

| Components | Carbo Bio Gel Sugar Coarse |
|---|---|
| Water (%) | 15.0-20.0 |
| Fructose (%) | 30.0-45.0 |
| Glucose (%) | 24.0-40.0 |
| Sucrose (%) | 0.1-4.8 |
| Maltodextrin (%) | 0.5-33.0 |
| Amino Acids and Proteins (mg/100 g) | 0.2-0.4 |
| Sodium (mg/100 g) | 1.6-17.0 |
| Zinc (mg/100 g) | 0.007-0.1 |
| Potassium (mg/100 g) | 0.47-8.1 |
| Magnesium (mg/100 g) | 0.26-3.25 |
| Calcium (mg/100 g) | 10.6-121.4 |
| Iron (mg/100 g) | 0.08-0.9 |

It is worth stressing that, with a sucrose inversion using resins, the initial syrup must have a maximum concentration of 60° Brix due to the need for fluidity in resin columns for removal of color and odor, as, with a higher concentration, there is no sufficient reactive activity in the resins. Another disadvantage from this method is the need for syrup concentration after the inversion reaction on the bed of the resin column, since the syrup needs to be heated up again, with a risk that undesired substances will form such as: furfural, hydromethylfurfural, and sulfooxymethylfurfural, which can even form during the acid process of inversion on the resin bed [Ogando F I B. Estudo da degradação térmica de sacarose e da contaminação microbiológica no processo de fabricação de açúcar. Master's Theses, ESALQ/USP, 2015; Rodrigues M V N. Otimização da produção do xarope de açúcar invertido através do use de resinas de troca-iônica. Master's Dissertation, Unicamp, 1998].

Example 5—Carbo Bio Gel Production from VHP or VVHP Sugar

1. Solid VVHP (Very Very High Polarization) or VHP (Very High Polarization) sucrose is diluted with water to a sucrose syrup at 78.0° Brix and heated at 80° C. for total dissolution of the sugar, through agitation in the tank;

2. The syrup is inverted CHEMICALLY (organic or non-organic products) or ENZYMATICALLY or using RESINS as described in the previous examples;

3. The syrup is filtered for removal of particulates;

4. The filtered syrup can be added with maltodextrin as shown in example 1.

Thus, EXAMPLE 5 refers to:

Using VHP or VVHP sugars (organic or not) as a basis for the Carbo Bio Gel product;

inverted CHEMICALLY, ENZYMATICALLY, or using RESINS at different rates of inversion (sucrose:glucose:fructose ratio preferably with an inversion of sucrose at 90% to 98% (w/w));

added with MALTODEXTRIN (from corn, cassava, or sweet potato, either GMO-free or conventional).

TABLE 7

Example of Carbo Bio Gel composition based on inverted VHP or VVHP sugars and their natural minerals.

| Components | Carbo Bio Gel VHP Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Amino Acids and Proteins (mg/100 g) | 3.5 |
| Sodium (mg/100 g) | 1.4-12.1 |
| Zinc (mg/100 g) | 0.07-0.35 |
| Potassium (mg/100 g) | 13.5-143.7 |
| Magnesium (mg/100 g) | 4.56-34.1 |
| Calcium (mg/100 g) | 10.8-29.5 |
| Iron (mg/100 g) | 0.5-6.1 |

Example 6—Carbo Bio Gel Production from Demerara Sugar

1. Solid Demerara sucrose is diluted with water to a sucrose syrup at 78.0° Brix and heated at 80° C. for total dissolution of the sugar, through agitation in the tank;

2. The syrup is CHEMICALLY inverted (organic or non-organic products) or ENZYMATICALLY or using RESINS as described in the previous examples;

3. The syrup is filtered for removal of particulates;

4. The filtered syrup can be added with maltodextrin as shown in example 1.

Thus, EXAMPLE 6 refers to:

using DEMERARA sugars (organic or not) as a basis for the Carbo Bio Gel product;

inverted CHEMICALLY, ENZYMATICALLY, or using RESINS at different rates of inversion (sucrose:glucose:fructose ratio preferably with an inversion of sucrose at 90% to 98% (w/w));

added with MALTODEXTRIN (from corn, cassava, or sweet potato, either GMO-free or conventional).

TABLE 8

Example of Carbo Bio Gel composition based on inverted Demerara sugar and their natural minerals.

| Components | Carbo Bio Gel Demerara Sugar |
|---|---|
| Water (%) | 15.0-20.0 |
| Fructose (%) | 30.0-45.0 |
| Glucose (%) | 24.0-40.0 |
| Sucrose (%) | 0.1-4.8 |
| Maltodextrin (%) | 0.5-33.0 |
| Amino Acids and Proteins (mg/100 g) | 2.33-4.94* |
| Sodium (mg/100 g) | 8.73-9.63* |
| Zinc (mg/100 g) | 0.009-0.036 |
| Potassium (mg/100 g) | 1.4-4.9 |
| Magnesium (mg/100 g) | 1.2-7.9 |
| Calcium (mg/100 g) | 8.02-24.42 |
| Iron (mg/100 g) | 0.33-5.78 |

*Faria [Faria DAM. Estudo Nutricional e sensorial de açúcares cristal, refinado, demerara e mascavo orgânicos e convencionais. Master's Thesis. UFSCAR, 2012].

Example 7—Carbo Bio Gel Production from Brown Sugar

1. Solid Brown sugar is diluted with water to a sucrose syrup at 78.0° Brix and heated at 80° C. for total dissolution of the sugar, through agitation in the tank;

2. The syrup is inverted CHEMICALLY (organic or non-organic products) or ENZYMATICALLY or using RESINS as described in the previous examples;

3. The syrup is filtered for removal of particulates;

4. The filtered syrup can be added with maltodextrin as shown in example 1.

Thus, EXAMPLE 7 refers to:

using Brown Sugar (organic or not) as a basis for the Carbo Bio Gel product;

inverted CHEMICALLY, ENZYMATICALLY, or using RESINS at different rates of inversion (sucrose:glucose:fructose ratio preferably with an inversion of sucrose at 90% to 98% (w/w));

added with MALTODEXTRIN (from corn, cassava, or sweet potato, either GMO-free or conventional).

TABLE 9

Example of Carbo Bio Gel composition based on inverted Brown sugar and its natural minerals.

| Components | Carbo Bio Gel Brown Sugar |
|---|---|
| Water (%) | 15.0-20.0 |
| Fructose (%) | 30.0-45.0 |
| Glucose (%) | 24.0-40.0 |
| Sucrose (%) | 0.1-4.8 |
| Maltodextrin (%) | 0.5-33.0 |
| Amino Acids and Proteins (mg/100 g) | 15.16* |
| Sodium (mg/100 g) | 116.1* |
| Zinc (mg/100 g) | 0.105-0.56 |
| Potassium (mg/100 g) | 43.98-289.15 |
| Magnesium (mg/100 g) | 17.58-106.55 |
| Calcium (mg/100 g) | 27.5-234.6 |
| Iron (mg/100 g) | 22.35-29.82 |

*Faria [Faria DAM. Estudo Nutricional e sensorial de açúcares cristal, refinado, demerara e mascavo orgânicos e convencionais. Master's Thesis. UFSCAR, 2012].

As shown in the previous examples, the basis for the Carbo Bio Gel product is an inverted syrup of sugarcane carbohydrates and may be added with Maltodextrin. From this common basis, all subsequent formulations can be produced, according to the subsequent examples:

Example 8—Carbo Bio Gel Production from the Sugars: Coarse, VHP, VVHP, Demerara, or Brown Added with Minerals 1. Solid sucrose from any type of sugar is diluted with water to a sucrose syrup at 78.0° Brix and heated at 80° C. for total dissolution of the sugar, through agitation in the tank;
2. The syrup is CHEMICALLY inverted (organic or non-organic products) or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with an additive taking as a reference the range for daily mineral intake for Zinc, Calcium, Phosphorus, Iron, Potassium, and Magnesium indicated for the various age groups or other groups of necessities as per the ANVISA's regulation approved under Decree No. 3029 dated Apr. 16, 1999, combined with art. 111, item I, letter "e" of the Internal Bylaws approved under Ordinance No. 593, dated Aug. 25, 2000, published in the Dec. 22, 2000 DOU (Federal Official Gazette), at a meeting held on Dec. 6, 2004. Other national or foreign regulations may also be used as a reference. Also, other minerals, such as copper, selenium, manganese and boron, vanadium, iodine, and chromium may be added within the limits established in the various regulations; Sodium and sodium phosphate may be supplemented within the adequate limits for use by athletes, as indicated in the state of the art. For instance, for sodium, the indication may be 210 mg/100 g of Carbo.

Thus, EXAMPLE 8 refers to:

using the organic or non-organic sugars: Coarse, VHP, VVHP, Demerara, or Brown as a basis for the Carbo Bio Gel product;

inverted CHEMICALLY, ENZYMATICALLY, or using RESINS at different rates of inversion;

added with MALTODEXTRIN (from corn, cassava, or sweet potato, either GMO-free or conventional);

Enriched with MINERALS.

TABLE 10

Example of Carbo Bio Gel composition based on inverted Demerara sugar and its additives. Example with 100% of the Anvisa-recommended dose.

| Components | Carbo Bio Gel Demerara Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Amino Acids and Proteins (mg/100 g) | 2.33-4.94* |
| Sodium (mg/100 g) | 210.0 |
| Zinc (mg/100 g/day) | Up to 7.0 |
| Potassium (mg/100 g) | 1.4-4.9 |
| Magnesium (mg/100 g/day) | Up to 260.0 |
| Calcium (mg/100 g/day) | Up to 1000.0 |
| Iron (mg/100 g/day) | Up to 14.0 |
| Phosphorus (mg/100 g/day) | Up to 700.0 |

*Faria [Faria DAM. Estudo Nutricional e sensorial de açúcares cristal, refinado, demerara e mascavo orgânicos e convencionais. Master's Thesis. UFSCAR, 2012].

Example 9—VHP Carbo Bio Gel Production from the Sugars: Coarse, VHP, VVHP, Demerara, or Brown Enriched with Fibers, Minerals, and Vitamins 1. Solid sucrose from any type of sugar is diluted with water to a sucrose syrup at 78.0° Brix and heated at 80° C. for total dissolution of the sugar, through agitation in the tank;
2. The syrup is inverted CHEMICALLY, ENZYMATICALLY, or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with an additive taking as a reference the range for daily intake for vitamins (RDI) from the complexes A, B, C, D, and E, folic acid, riboflavin, thiamine, and niacin, as indicated for the various age groups or group of necessities as per the ANVISA's regulation approved under Decree No. 3029 dated Apr. 16, 1999, combined with art. 111, item I, letter "e" of the Internal Bylaws approved under Ordinance No. 593, dated Aug. 25, 2000, published in the Dec. 22, 2000 DOU at a meeting held on Dec. 6, 2004. Other national or foreign regulations may also be used as a reference. Other vitamins, such as vitamin B5—pantothenic acid, and vitamin K, may be added according to the various regulations. Formulations with higher quantities than the RDI may be prepared seeking to boost the Carbo Bio Gel product, such as adding vitamin C at 1,000 mg/100 g of the product.

Thus, EXAMPLE 9 refers to:

using the organic or non-organic sugars: Coarse, VHP, VVHP, Demerara, or Brown as a basis for the Carbo Bio Gel product;

inverted CHEMICALLY, ENZYMATICALLY, or using RESINS at different rates of inversion;

added with MALTODEXTRIN (from corn, cassava, or sweet potato, either GMO-free or conventional);

Enriched with MINERALS;

Enriched with VITAMINS.

TABLE 11

Example of Carbo Bio Gel composition based on inverted Demerara sugar and its additives. Example with 100% of the Anvisa-recommended dose.

| Components | Carbo Bio Gel Demerara Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Amino Acids and Proteins (mg/100 g) | 2.33-4.94 |
| Sodium (mg/100 g) | 210.0 |
| Zinc (mg/100 g/day) | Up to 7.0 |
| Potassium (mg/100 g) | 1.4-4.9 |
| Magnesium (mg/100 g/day) | Up to 260.0 |
| Calcium (mg/100 g/day) | Up to 1000.0 |
| Iron (mg/100 g/day) | Up to 14.0 |
| Phosphorus (mg/100 g/day) | Up to 700.0 |
| Vitamin A (mg/100 g/day) | Up to 0.6 |
| B1 - Thiamine (mg/100 g/day) | Up to 1.2 |
| B2 - Riboflavin (mg/100 g/day) | Up to 1.3 |
| B3 - Niacin (mg/100 g/day) | Up to 16.0 |
| B5 - Calcium Pantothenate | Up to 5.0 |

TABLE 11-continued

Example of Carbo Bio Gel composition based on inverted Demerara sugar and its additives. Example with 100% of the Anvisa-recommended dose.

| Components | Carbo Bio Gel Demerara Sugar |
|---|---|
| B6 - Pyridoxine (mg/100 g/day) | Up to 1.3 |
| B9 - Folic acid (mg/100 g/day) | Up to 0.4 |
| B12 - cobalamin (µg/100 g/day) | Up to 2.4 |
| Vitamins C (mg/100 g/day) | Up to 1000.0 |
| Vitamins D (mg/100 g/day) | Up to 0.005 |
| Vitamins E (mg/100 g/day) | Up to 10.0 |

It is worth highlighting that, in order to preserve the vitamins naturally coming from the sugars, the enzymatic inversion method is the preferred one, since the conventional chemical inversion or the one following the positive organic list or even using resins may degrade the vitamins due to the aggressiveness of the chemical reaction. Adding vitamins up to the RDI, as proposed in this example, is a process always done after the sugar inversion, which therefore mitigates the risk of vitamin degradation.

Example 10—Carbo Bio Gel Production from the Sugars: Coarse, VHP, VVHP, Demerara, or Brown Enriched with Minerals, Vitamins, and Amino Acids 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY, ENZYMATICALLY, or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids, precursors, and byproducts such as: BCAA complex, complex of several amino acids, or isolated amino acids, such as: glutamic acid, aspartic acid, glutamine, histidine, glycine, threonine, alanine, arginine, agmatine, citrulline, proline, tyrosine, valine, methionine, cysteine, n-acetylcysteine, leucine, β-hydroxy-β-methylbutyrate, phenylalanine, isoleucine, tryptophan, ornithine, and lysine, and others. This addition can be done with isolated amino acids, complex of amino acids, creatine (glycine, L-arginine, and L-methionine), taurine, and carnitine, as per the current state of the art. As already exposed in the state of the art, addition of amino acids is of great interest.

Table 12 shows the main amino acids that can be added to Carbo Bio Gel.

Thus, EXAMPLE 10 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS.

TABLE 12

Example of Carbo Bio Gel composition based on inverted Demerara sugar and its additives.

| Components | Carbo Bio Gel Demerara Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Sodium (mg/100 g) | 210.0 |
| Zinc (mg/100 g/day) | Up to 7.0 |
| Potassium (mg/100 g) | 13.5-143.7 |
| Magnesium (mg/100 g/day) | Up to 260.0 |
| Calcium (mg/100 g/day) | Up to 1000.0 |
| Iron (mg/100 g/day) | Up to 14.0 |
| Phosphorus (mg/100 g/day) | Up to 700.0 |
| Vitamin A (mg/100 g/day) | Up to 0.6 |
| B1 - Thiamine (mg/100 g/day) | Up to 1.2 |
| B2 - Riboflavin (mg/100 g/day) | Up to 1.3 |
| B3 - Niacin (mg/100 g/day) | Up to 16.0 |
| B5 - Calcium Pantothenate (mg/100 g/day) | Up to 5.0 |
| B6 - Pyridoxine (mg/100 g/day) | Up to 1.3 |
| B9 - Folic acid (mg/100 g/day) | Up to 0.4 |
| B12 - cobalamin (µg/100 g/day) | Up to 2.4 |
| Vitamins C (mg/100 g/day) | Up to 45.0 |
| Vitamins D (mg/100 g/day) | Up to 0.005 |
| Vitamins E (mg/100 g/day) | Up to 10.0 |
| Leucine (mg/kg of weight/day) | 20.0-40.0 |
| Isoleucine (mg/kg of weight/day) | 10.0-25.0 |
| Valine (mg/kg of weight/day) | 20.0-40.0 |
| BCAA (valine + isoleucine + leucine) (g/day) | 4.0 to 21.0 |
| Arginine (mg/day) | 1500-5000 |
| Glutamine (g/day) | 20-30 |
| Alanine (g/day) | 1.0-6 |
| Creatine (g/day) | 0.03-0.5 |
| Taurine (mg/100 mL) | Up to 400 |
| Carnitine (g/day) | Up to 6 g |

It is worth highlighting that, in order to preserve the amino acids naturally coming from the sugars, the enzymatic inversion method is the preferred one, since the chemical or conventional inversion or the one following the positive organic list or even using resins may degrade the amino acids due to the aggressiveness of the chemical reaction. Adding vitamins up to the RDI, as proposed in this example, is a process always done after the sugar inversion, which therefore mitigates the risk of their degradation.

Example 11—Carbo Bio Gel Production from the Sugars: Coarse, VHP, VVHP, Demerara, or Brown Enriched with Minerals, Vitamins, Amino Acids, and Encapsulated Substances 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY, ENZYMATICALLY, or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;

7. The Carbo Bio Gel syrup can be added with several types of amino acids as described in example 10;
8. The Carbo Bio Gel syrup can be added with encapsulated, micro-encapsulated, or nano-encapsulated substances, for instance, sugarcane molasse, sugarcane honey, pharmacological and nutraceutical compounds, natural plant extracts, plant-based oils, various carbohydrates, as described in the state of the art, but not limited to these. The encapsulation process preserves the pharmacological properties of products and masks their potential interferences in the organoleptic properties of Carbo Bio Gel; however, it maintains their functional properties intact. The addition proportion will depend on the type of product to be added and the concentration of the substances of interest, between 1.0 to 10.0% of the Carbo Bio Gel syrup, though it can be higher. Some additives like vitamins, amino acids, and minerals may also be encapsulated.

Thus, EXAMPLE 11 refers to:

using the organic or non-organic sugars: Coarse, VHP, VVHP, Demerara, or Brown as a basis for the Carbo Bio Gel product;

inverted CHEMICALLY or ENZYMATICALLY or using RESINS inverted at different inversion rates (sucrose/glucose+fructose ratio from 0 to 98% inversion);

added with MALTODEXTRIN (from corn, cassava, or sweet potato, either GMO-free or conventional);

Enriched with MINERALS;

Enriched with VITAMINS;

Enriched with AMINO ACIDS;

Enriched with ENCAPSULATED SUBSTANCES.

TABLE 13

Example of Carbo Bio Gel composition based on inverted Demerara sugar and its additives.

| Components | Carbo Bio Gel Demerara Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Encapsulated substances (%) | 1.0-10.0% |
| Sodium (mg/100 g) | 210.0 |
| Zinc (mg/100 g/day) | Up to 7.0 |
| Potassium (mg/100 g) | 13.5-143.7 |
| Magnesium (mg/100 g/day) | Up to 260.0 |
| Calcium (mg/100 g/day) | Up to 1000.0 |
| Iron (mg/100 g/day) | Up to 14.0 |
| Phosphorus (mg/100 g/day) | Up to 700.0 |
| Vitamin A (mg/100 g/day) | Up to 0.6 |
| B1 - Thiamine (mg/100 g/day) | Up to 1.2 |
| B2 - Riboflavin (mg/100 g/day) | Up to 1.3 |
| B3 - Niacin (mg/100 g/day) | Up to 16.0 |
| B5 - Calcium Pantothenate (mg/100 g/day) | Up to 5.0 |
| B6 - Pyridoxine (mg/100 g/day) | Up to 1.3 |
| B9 - Folic acid (mg/100 g/day) | Up to 0.4 |
| B12 - cobalamin (μg/100 g/day) | Up to 2.4 |
| Vitamins C (mg/100 g/day) | Up to 45.0 |
| Vitamins D (mg/100 g/day) | Up to 0.005 |
| Vitamins E (mg/100 g/day) | Up to 10.0 |
| Leucine (mg/kg of weight/day) | 20.0-40.0 |
| Isoleucine (mg/kg of weight/day) | 10.0-25.0 |
| Valine (mg/kg of weight/day) | 20.0-40.0 |
| BCAA (valine + isoleucine + leucine) (g/day) | 4.0 to 21.0 |
| Arginine (mg/day) | 1500-5000 |
| Glutamine (g/day) | 20-30 |
| Alanine (g/day) | 1.0-6 |

TABLE 13-continued

Example of Carbo Bio Gel composition based on inverted Demerara sugar and its additives.

| Components | Carbo Bio Gel Demerara Sugar |
|---|---|
| Creatine (g/day) | 0.03-0.5 |
| Taurine (mg/100 mL) | Up to 400 |
| Carnitine (g/day) | Up to 6 g |

Example 12—Carbo Bio Gel Production from the Sugars: Coarse, VHP, VVHP, Demerara, or Brown Enriched with Minerals, Vitamins, Amino Acids, Encapsulated Substances, and Caffeine 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY, ENZYMATICALLY, or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine from 3 to 6 mg/kg of body weight or preferably at a concentration of 270 mg/100 g of caffeine:Carbo Bio Gel syrup. Other concentrations may be used as indicated.

Thus, EXAMPLE 12 refers to:

using the organic or non-organic sugars: Coarse, VHP, VVHP, Demerara, or Brown as a basis for the Carbo Bio Gel product;

inverted CHEMICALLY, ENZYMATICALLY, or using RESINS at different rates of inversion;

added with MALTODEXTRIN (from corn, cassava, or sweet potato, either GMO-free or conventional);

Enriched with MINERALS; Enriched with VITAMINS; Enriched with AMINO ACIDS;

Enriched with ENCAPSULATED SUBSTANCES; Enriched with CAFFEINE.

TABLE 14

Example of Carbo Bio Gel composition based on inverted Demerara sugar and its additives.

| Components | Carbo Bio Gel Demerara Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Encapsulated substances (%) | 1.0-10.0% |
| Caffeine (mg/100 g) | 270.0 |
| Sodium (mg/100 g) | 210.0 |
| Zinc (mg/100 g/day) | Up to 7.0 |
| Potassium (mg/100 g) | 13.5-143.7 |
| Magnesium (mg/100 g/day) | Up to 260.0 |

TABLE 14-continued

Example of Carbo Bio Gel composition based on inverted Demerara sugar and its additives.

| Components | Carbo Bio Gel Demerara Sugar |
|---|---|
| Calcium (mg/100 g/day) | Up to 1000.0 |
| Iron (mg/100 g/day) | Up to 14.0 |
| Phosphorus (mg/100 g/day) | Up to 700.0 |
| Vitamin A (mg/100 g/day) | Up to 0.6 |
| B1 - Thiamine (mg/100 g/day) | Up to 1.2 |
| B2 - Riboflavin (mg/100 g/day) | Up to 1.3 |
| B3 - Niacin (mg/100 g/day) | Up to 16.0 |
| B5 - Calcium Pantothenate (mg/100 g/day) | Up to 5.0 |
| B6 - Pyridoxine (mg/100 g/day) | Up to 1.3 |
| B9 - Folic acid (mg/100 g/day) | Up to 0.4 |
| B12 - cobalamin (µg/100 g/day) | Up to 2.4 |
| Vitamins C (mg/100 g/day) | Up to 45.0 |
| Vitamins D (mg/100 g/day) | Up to 0.005 |
| Vitamins E (mg/100 g/day) | Up to 10.0 |
| Leucine (mg/kg of weight/day) | 20.0-40.0 |
| Isoleucine (mg/kg of weight/day) | 10.0-25.0 |
| Valine (mg/kg of weight/day) | 20.0-40.0 |
| BCAA (valine + isoleucine + leucine) (g/day) | 4.0 to 21.0 |
| Arginine (mg/day) | 1500-5000 |
| Glutamine (g/day) | 20-30 |
| Alanine (g/day) | 1.0-6 |
| Creatine (g/day) | 0.03-0.5 |
| Taurine (mg/100 mL) | Up to 400 |
| Carnitine (g/day) | Up to 6 g |

Example 13—Carbo Bio Gel Production from the Sugars: Coarse, VHP, VVHP, Demerara, or Brown Enriched with Minerals, Vitamins, Amino Acids, Encapsulated Substances, Caffeine, and Proteins 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY, ENZYMATICALLY, or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins: whey protein concentrate, whey protein isolate, and whey protein hydrolysate, casein, and plant-based proteins (soy, rice, peas, quinoa, etc.), animal proteins from egg, bovine colostrum, and others, as described in the state of the art. The indicated concentrations range from 5 to 20 g/day of consumption by a normal adult and may be higher upon professional instruction or different formulation.

Thus, EXAMPLE 13 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS.

TABLE 15

Example of Carbo Bio Gel composition based on inverted Demerara sugar and its additives.

| Components | Carbo Bio Gel Demerara Sugar |
|---|---|
| Water (%) | 15.0-20.0 |
| Fructose (%) | 30-45.0 |
| Glucose (%) | 24-40.0 |
| Sucrose (%) | 0.1-4.8 |
| Maltodextrin (%) | 0.5-33.0 |
| Encapsulated substances (%) | 1.0-10.0% |
| Caffeine (mg/100 g) | 270.0 |
| Sodium (mg/100 g) | 210.0 |
| Zinc (mg/100 g/day) | Up to 7.0 |
| Potassium (mg/100 g) | 13.5-143.7 |
| Magnesium (mg/100 g/day) | Up to 260.0 |
| Calcium (mg/100 g/day) | Up to 1000.0 |
| Iron (mg/100 g/day) | Up to 14.0 |
| Phosphorus (mg/100 g/day) | Up to 700.0 |
| Vitamin A (mg/100 g/day) | Up to 0.6 |
| B1 - Thiamine (mg/100 g/day) | Up to 1.2 |
| B2 - Riboflavin (mg/100 g/day) | Up to 1.3 |
| B3 - Niacin (mg/100 g/day) | Up to 16.0 |
| B5 - Calcium Pantothenate (mg/100 g/day) | Up to 5.0 |
| B6 - Pyridoxine (mg/100 g/day) | Up to 1.3 |
| B9 - Folic acid (mg/100 g/day) | Up to 0.4 |
| B12 - Cobalamin (µg/100 g/day) | Up to 2.4 |
| Vitamins C (mg/100 g/day) | Up to 45.0 |
| Vitamins D (mg/100 g/day) | Up to 0.005 |
| Vitamins E (mg/100 g/day) | Up to 10.0 |
| Leucine (mg/kg of weight/day) | 20.0-40.0 |
| Isoleucine (mg/kg of weight/day) | 10.0-25.0 |
| Valine (mg/kg of weight/day) | 20.0-40.0 |
| BCAA (valine + isoleucine + leucine) (g/day) | 4.0 to 21.0 |
| Arginine (mg/day) | 1500-5000 |
| Glutamine (g/day) | 20-30 |
| Alanine (g/day) | 1.0-6 |
| Creatine (g/day) | 0.03-0.5 |
| Taurine (mg/100 mL) | Up to 400 |
| Carnitine (g/day) | Up to 6 g |
| Whey Protein concentrate (g/day) | 10.0-20.0 |
| Whey Protein isolate (g/day) | 5.0-20.0 |
| Whey Protein hydrolysate (g/day) | 5.0-20.0 |
| Soy protein (g/day) | 10.0-20.0 |
| Casein (g/day) | 5.0-20.0 |

Example 14—Carbo Bio Gel Production from the Sugars: Coarse, VHP, VVHP, Demerara, or Brown Enriched with Minerals, Vitamins, Amino Acids, Encapsulated Substances, Caffeine, Proteins, and Aromas 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY, ENZYMATICALLY, or using RESINS as described in the previous examples;
3. The syrup is filtered for removal of particulates;

4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized with a natural aroma, either identical to the natural scent or artificial, seeking to bring the product several types of flavors, such as: honey, vanilla, orange, passion fruit, guarana, acai, lemon, chocolate, tutti-frutti, blackberry, etc., but not limited to these.

Thus, EXAMPLE 14 refers to:
using the organic or non-organic sugars: Coarse, VHP, VVHP, Demerara, or Brown as a basis for the Carbo Bio Gel product;
inverted CHEMICALLY or ENZYMATICALLY or using RESINS inverted at different inversion rates (sucrose/glucose+fructose ratio from 0 to 98% inversion);
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas.

Example 15—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, and Other Carbohydrates 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY, ENZYMATICALLY, or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;
12. The Carbo Bio Gel syrup can be enriched with other carbohydrates, such as fructose, dextrose, lactose, sorbitol, erythritol, xylitol, maltose, mannose, mannitol, natural fruit syrup (e.g. apple syrup), coconut sugar, beetroot syrup, fructooligosaccharides (FOS), palatinose (isomaltulose), leucrose, xylose, trehalose, cellobiose, arabinose, cyclodextrins, chitins and chitosans, and royal jelly, and others, at different concentrations. For example, the Carbo Bio Gel syrup containing 2 glucose parts and 1 fructose part (2 glucose: 1 fructose). To obtain lower sweetness in the product, but keep the energy content preserved. The enrichment proportion can be 0.5 to 50.0% of the product.

Thus, EXAMPLE 15 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS; Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES.

Example 16—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, Other Carbohydrates, and Organic Extracts 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;

12. The Carbo Bio Gel syrup can be enriched with several carbohydrates, as described in example 15;
13. The Carbo Bio Gel syrup can be enriched with organic extracts from a plant or animal source. Extract from plants rich in plant steroids, flavonoids, and triterpenes, extract from algae, plants capable of inducing the testosterone levels, in addition to extracts with pharmacological and therapeutic functions known as: ginger, cinnamon, passion fruit, blueberry, pomegranate, guaco, green tea, ginseng, guarana, etc., seeking to add the supplement/foodstuff with thermogenic, digestive, anti-inflammatory, anxiolytic, diuretic, and other properties. Other extracts, such as extracts from propolis and its byproducts, may be used. Each different extract has its indication and dosage and must be supplemented as instructed in pharmacopoeias and phytotherapeutic formulations.

Thus, EXAMPLE 16 refers to:
using the organic or non-organic sugars: Coarse, VHP, VVHP, Demerara, or Brown as a basis for the Carbo Bio Gel product;
inverted CHEMICALLY or ENZYMATICALLY or using RESINS inverted at different inversion rates (sucrose/glucose+fructose ratio from 0 to 98% inversion);
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES;
Enriched with ORGANIC EXTRACTS.

Example 17—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, Other Carbohydrates, Organic Extracts, and Sodium Bicarbonate 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;
12. The Carbo Bio Gel syrup can be enriched with several carbohydrates, as described in example 15;
13. The Carbo Bio Gel syrup can be enriched with organic extracts as described in example 16;
14. The syrup can be enriched with sodium bicarbonate in a proportion of 0.01 g to 1.0 g per kg of body weight or preferably with 5 g added to a 30 g dose of the supplement/foodstuff.

Thus, EXAMPLE 17 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES;
Enriched with ORGANIC EXTRACTS;
Enriched with SODIUM BICARBONATE.

Example 18—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, Other Carbohydrates, Organic Extracts, Sodium Bicarbonate, and Fatty Acids 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;
12. The Carbo Bio Gel syrup can be enriched with several carbohydrates, as described in example 15;

13. The Carbo Bio Gel syrup can be enriched with organic extracts as described in example 16;
14. The syrup can be enriched with sodium bicarbonate as described in example 17;
15. The syrup can be enriched with short-chain fatty acids, such as acetate, propionate, and butyrate, coconut oil, palm oil; medium- and long-chain acids present in olive, canola, sunflower, soy, safflower, corn, and peanut oils, safflower and fish oil, as per the concentration indication for each fatty acid, according to the state of the art. For example, for safflower oil, the indication is 1 g/day.

Thus, EXAMPLE 18 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES;
Enriched with ORGANIC EXTRACTS;
Enriched with SODIUM BICARBONATE;
Enriched with FATTY ACID.

Example 19—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, Other Carbohydrates, Organic Extracts, Sodium Bicarbonate, Fatty Acids, and Phosphatidic Acid 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;
12. The Carbo Bio Gel syrup can be enriched with several carbohydrates, as described in example 15;
13. The Carbo Bio Gel syrup can be enriched with organic extracts as described in example 16;
14. The Carbo Bio Gel syrup can be enriched with sodium bicarbonate as described in example 17;
15. The syrup can be enriched with chain fatty acids as described in example 18;
16. The syrup can be enriched with phosphatidic acid at many concentrations, for instance, 750 mg/day, or as indicated, but not limited to this concentration.

Thus, EXAMPLE 19 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES;
Enriched with ORGANIC EXTRACTS;
Enriched with SODIUM BICARBONATE;
Enriched with FATTY ACIDS;
Enriched with PHOSPHATIDIC ACID.

Example 20—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, Other Carbohydrates, Organic Extracts, Sodium Bicarbonate, Fatty Acids, Phosphatidic Acid, and Related Items 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;

12. The Carbo Bio Gel syrup can be enriched with several carbohydrates, as described in example 15;
13. The Carbo Bio Gel syrup can be enriched with organic extracts as described in example 16;
14. The Carbo Bio Gel syrup can be enriched with sodium bicarbonate as described in example 17;
15. The syrup can be enriched with chain fatty acids as described in example 18;
16. The syrup can be enriched with chain phosphatidic acid as described in example 19;
17. The syrup can be enriched with enzymes such as Coenzyme Q10, creatine kinase, catalase, lactate-dehydrogenase, using the enzymatic inhibitor allopurinol, and others. The concentration indication differs for each enzyme, according to the state of the art. For example, for coenzyme Q10, the indicated dosage is 300 mg/day.

Thus, EXAMPLE 20 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES;
Enriched with ORGANIC EXTRACTS;
Enriched with SODIUM BICARBONATE;
Enriched with FATTY ACIDS;
Enriched with PHOSPHATIDIC ACID;
Enriched with ENZYMES.

Example 21—Carbo Bio Gel Production from the Sugars: Coarse, VHP, VVHP, Demerara, or Brown Enriched with Minerals, Vitamins, Amino Acids, Encapsulated Substances, Caffeine, Proteins, Aromas, Other Carbohydrates, Organic Extracts, Sodium Bicarbonate, Fatty Acids, Phosphatidic Acid, Enzymes, and Calcium Pyruvate 1. Solid sucrose from any type of sugar is diluted with water to a sucrose syrup at 78.0° Brix and heated at 80° C. for total dissolution of the sugar, through intensive agitation in the tank;
2. The syrup is inverted CHEMICALLY or ENZYMATICALLY or using RESINS as described in the previous examples;
3. The syrup is filtered for removal of particulates;
4. The filtered syrup can be added with maltodextrin as described in the previous examples;
5. The Carbo Bio Gel syrup can be added with minerals as described in example 8;
6. The Carbo Bio Gel syrup can be added with vitamins as described in example 9;
7. The Carbo Bio Gel syrup can be added with several types of amino acids as described in example 10;
8. The Carbo Bio Gel syrup can be added with encapsulated, micro-encapsulated, or nano-encapsulated substances as described in example 11;
9. The Carbo Bio Gel syrup can be added with caffeine as described in example 12;
10. The Carbo Bio Gel syrup can be added with proteins as described in example 13;
11. The Carbo Bio Gel syrup can be aromatized as described in example 14;
12. The Carbo Bio Gel syrup can be enriched with several carbohydrates, as described in example 15;
13. The Carbo Bio Gel syrup can be enriched with organic extracts as described in example 16;
14. The Carbo Bio Gel syrup can be enriched with sodium bicarbonate as described in example 17;
15. The syrup can be enriched with chain fatty acids as described in example 18;
16. The syrup can be enriched with chain phosphatidic acid as described in example 19;
17. The syrup can be enriched with enzymes as described in example 20;
18. The syrup can be enriched with calcium pyruvate at several concentrations, such as 0.1 g/Kg of body weight/day for athletes, or as professionally instructed.

Thus, EXAMPLE 21 refers to:
using the organic or non-organic sugars: Coarse, VHP, VVHP, Demerara, or Brown as a basis for the Carbo Bio Gel product;
inverted CHEMICALLY, ENZYMATICALLY, or using RESINS at different rates of inversion;
added with MALTODEXTRIN (from corn, cassava, or sweet potato, either GMO-free or conventional);
Enriched with MINERALS;
Enriched with VITAMINS;
Enriched with AMINO ACIDS;
Enriched with ENCAPSULATED SUBSTANCES;
Enriched with CAFFEINE;
Enriched with PROTEINS;
Aromatized with NATURAL AROMA, IDENTICAL TO THE NATURAL SCENT OR ARTIFICIAL, with different aromas;
Enriched with different CARBOHYDRATES;
Enriched with ORGANIC EXTRACTS;
Enriched with SODIUM BICARBONATE;
Enriched with FATTY ACIDS;
Enriched with PHOSPHATIDIC ACID;
Enriched with ENZYMES;
Enriched with CALCIUM PYRUVATE.

Example 22—Carbo Bio Gel Production from the Sugars in Examples 1 Through 21, with the Syrup Possibly Added with Alginate and Encapsulating Substances Aiming at Encapsulation and Production of Carbo Bio Gel Pearls The Carbo Bio Gel product, whether or not added with ergogenic products, can be encapsulated using several products, such as calcium alginate, alginic acid, maltodextrin, and modified starches producing capsules or pearls of several diameters, not limited to only these encapsulation agents.

As an example, calcium alginate, which is the main gel used for encapsulation, because of its gelling properties, low cost, handiness, and inexistent toxicity, will be described below:

1. The Carbo Bio Gel syrup may be added with 5.0% (w/w) acid alginate heated at 70° C. The concentration of alginate may vary between 1.0 and 20.0% in the product;
2. The Carbo Bio Gel syrup is dripped into a water-based solution containing CaCl2 through agitation at 100 rpm, using mechanical dripping devices that can drip several volumes, consequentially producing product pearls of several diameters;
3. The pearls can be sunk in the solution for different times, as one might want a softer or harder pearl, depending on the application.

Thus, the claim in EXAMPLE 22 refers to:

using the encapsulation technique for production of nano-, micro-, and macro-balls and pearls of Carbo Bio Gel syrup, added or not with ergogenic products;

using encapsulating products, such as calcium alginate, maltodextrin, and modified starches, but not limited to these, for production of encapsulated Carbo Bio Gel.

The Carbo Bio Gel pearls are in a shape never seen before on the market, thus bringing an innovation in the form and marketing of the product.

Example 23—Carbo Bio Gel Production from the Sugars in Examples 1 Through 21, with the Syrup Possibly Added with Thickeners and Gelling Agents with Aims to Obtain Carbo Bio Gel Gels and Pastes The Carbo Bio Gel product, whether or not added with ergogenic products, can be thickened using several hydrocolloids, such as Xanthan gum, Guar gum, pectins, gelatins, collagen, gellan gum, carrageenans, cellulose compounds, and others, like modified starches, gelling agents, and emulsifiers, producing Carbo Bio Gel gels and pastes with several textures, not limited to only said agents.

As an example, sodium carboxymethyl cellulose, which was used in the Carbo Bio Gel syrup, with a texturized gel being obtained, according to the examples:

1. The Carbo Bio Gel syrup may be added with 1.0% (w/w) sodium carboxymethyl cellulose, such as the product Walocel CRT 40000PA. The concentration of sodium carboxymethyl cellulose may vary between 0.1 and 20.0% (w/w) in the product. Sodium carboxymethyl cellulose can be added directly to the syrup and mechanically homogenized, producing a Carbo Bio Gel product with gelatinous texture;
2. The Carbo Bio Gel syrup can be added with 1.0% (w/w) modified starch and 0.75% (w/w) Xanthan gum. The concentration of these substances may vary between 0.1 and 20.0% (w/w) in the product at several proportions for the desired consistency;
3. The Carbo Bio Gel syrup can be added with 1.0% to 5% pectin and/or agar at many proportions. The concentration of these substances may vary between 0.1 and 20.0% (w/w) in the product at several proportions for the desired consistency;
4. The Carbo Bio Gel syrup can be added with 1.0% to 5% gelatin (collagen) at many proportions. The concentration of these substances may vary between 0.1 and 20.0% in the product at several proportions for the desired consistency;
5. The Carbo Bio Gel syrup can be added with 1.0% to 5% gellan gum and/or gellan gum blend and other gelling agents or thickeners at many proportions. The concentration of these substances may vary between 0.1 and 20.0% in the product at several proportions for the desired consistency;
6. Other consistencies may be obtained from using Xanthan gums and blends among these thickening and gelling agents.

Thus, the claim in EXAMPLE 23 refers to:

using thickeners, gelling agents, emulsifiers, hydrocolloids, modified starches, and cellulose compounds to obtain Carbo Bio Gel gels and pastes.

The Carbo Bio Gel gels and pastes exhibit a form of supply that is innovative on the market and meets the needs of athletes engaged in several sport modalities and supplementation needs, according to the state of the art.

In this regard, the scope of this invention also covers the various uses and applications of a Carbo Bio Gel composition to be used not only in sports, but also as a nutritional supplement.

The above examples have been described to illustrate the various methods of production and the vast myriad of possible compositions and formulations of Carbo Bio Gel relatively to the types of inversion, several types of raw materials, and additives, and must not be faced as limiting this invention, it being known that slight variations from the above will still be part of the scope of this invention.

The invention claimed is:

1. A preparation method for a food supplement comprising steps of:
    a) dissolving raw material including solid sucrose in water to obtain a 60-78.0° Brix syrup;
    b) heating the syrup to 80° C. for total sugar dissolution;
    c) inverting the sugar of the syrup by chemical or enzymatic means or using resins to fructose and glucose, wherein a sucrose inversion rate ranges from 90% to 98%, wherein the inverted syrup includes equimolar quantities of glucose and fructose and a concentration of sucrose is lower than concentrations of glucose and fructose; and
    d) adding maltodextrin;
    e) forming the food supplement comprising water: 15.0-20.0% (w/w); fructose: 30.0-45.0 (w/w); glucose: 30.0-40.0 (w/w); sucrose: 2.0-10.0 (w/w); and maltodextrin: 0.5-33.0 (w/w); with the supplement being perservative-free.

2. The method according to claim 1, wherein the raw material is chosen from a sugarcane sugar, brown sugar, VHP sugar, VVHP sugar, Demerara sugar, coarse sugar, and combinations thereof.

3. The method according to claim 1, wherein the chemical inversion step uses citric acid or phosphoric acid.

4. The method according to claim 1, wherein the enzymatical inversion step uses an invertase enzyme from a non-animal source, which can be, either natural or recombinant, extracted or isolated from micro-organisms bred in bioreactors, preferably using an invertase enzyme extracted from yeast without any kind of genetic modification.

5. The method according to claim 1, comprising concentrating the inverted sugar when a resin is used during the inversion step, with such concentration taking place before maltodextrin is added.

* * * * *